(12) United States Patent
Tachibana et al.

(10) Patent No.: US 7,271,188 B2
(45) Date of Patent: Sep. 18, 2007

(54) IMIDAZOLIDINE DERIVATIVES

(75) Inventors: Kazutaka Tachibana, Gotenba (JP);
Haruhiko Sato, Gotenba (JP);
Masateru Ohta, Gotenba (JP);
Mitsuaki Nakamura, Gotenba (JP);
Takuya Shiraishi, Gotenba (JP);
Ikuhiro Imaoka, Gotenba (JP); Hitoshi Yoshino, Gotenba (JP); Masahiro Nagamuta, Kita-ku (JP); Hiromitsu Kawata, Kamakura (JP)

(73) Assignee: Chugai Seikayu Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/560,281

(22) PCT Filed: Jun. 11, 2004

(86) PCT No.: PCT/JP2004/008211
§ 371 (c)(1),
(2), (4) Date: Dec. 12, 2005

(87) PCT Pub. No.: WO2004/111012
PCT Pub. Date: Dec. 23, 2004

(65) Prior Publication Data
US 2006/0135583 A1    Jun. 22, 2006

(30) Foreign Application Priority Data
Jun. 12, 2003 (JP) .............................. 2003-168267

(51) Int. Cl.
*A61K 31/4166* (2006.01)
*C07D 233/86* (2006.01)
*C07C 311/03* (2006.01)

(52) U.S. Cl. .................... 514/391; 548/320.1; 560/303

(58) Field of Classification Search ............. 548/301.7, 548/318.5, 320.1; 514/391; 560/129, 303
See application file for complete search history.

(56) References Cited

U.S. PATENT DOCUMENTS

| | | |
|---|---|---|
| 5,411,981 A | 5/1995 | Gaillard-Kelly et al. |
| 5,627,201 A | 5/1997 | Gaillard-Kelly et al. |
| RE35,956 E | 11/1998 | Gaillard-Kelly et al. |

FOREIGN PATENT DOCUMENTS

| | | |
|---|---|---|
| EP | 580459 A1 | 1/1994 |
| GB | 2118942 A1 | 4/1982 |
| JP | 58-194891 A | 11/1983 |
| JP | 4-308579 A | 10/1992 |
| JP | 6-73017 A | 3/1994 |
| JP | 10-510845 A | 10/1998 |
| JP | 02-528434 S | 9/2002 |
| WO | 0494819 A1 | 7/1992 |
| WO | WO97/00071 | 1/1997 |
| WO | WO 00/24710 | 5/2000 |
| WO | WO 03/093243 A1 | 11/2003 |

OTHER PUBLICATIONS

Isaacs et al, Androgen receptor outwits prostate cancer drugs, Jan. 2004, Nature Medicine, 10 (1), p. 26-27.*
Medical Encyclopedia: Englarged Prostrate, retrieved from internet on Jan. 6, 2007, URL: http://www.nlm.nih.gov/medlineplus/ency/article/000381.htm.*
Olsen et al, Evaluation and treatment of male and female pattern hair loss, Nov. 23, 2004, J. Am. Acad. Dermatol, p. 301-311.*
Prostate Cancer Teratment Options, retrieved from the Internet on Jan. 6, 2007, URL: http://familydoctor.org/264.xml?printxml.*
Fenton et al, Precocious Pseudopuberty, eMedicine, retrieved from Internet on Jan. 18, 2007, <http://www.emedicine.com/ped/topic1881.htm>, p. 1-18.*
Wong, Choi-iok, "Androgen Receptor Antagoinist versus Agonist Activities of the Fungicide Vinclozolin Relative to Hydroxyflutamide", vol. 270, No. 34, pp. 19998-20003, 1995.

* cited by examiner

*Primary Examiner*—Rebecca Anderson
*Assistant Examiner*—Karen Cheng
(74) *Attorney, Agent, or Firm*—Browdy and Neimark, PLLC

(57) ABSTRACT

The present invention provides a compound represented by formula (I):
[Formula 1]

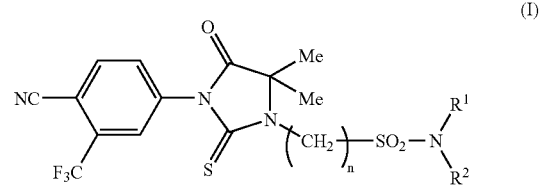

wherein n is an integer selected from 1 to 20, and $R^1$ and $R^2$, which may be the same or different, each represent a hydrogen atom, or a linear or branched $C_1$-$C_6$ alkyl group, or a salt, a prodrug or a solvate thereof, as well as a drug, a pharmaceutical composition containing the compound, and the like.

13 Claims, No Drawings

IMIDAZOLIDINE DERIVATIVES

FIELD OF THE INVENTION

The present invention relates to imidazolidine derivatives which have a substituted alkyl group in 3-position, and a drug containing these imidazolidine derivatives as an active ingredient.

BACKGROUND ART

It has been made clear in the past that the male hormone androgen plays an important role in prostate cancer, benign prostatic hypertrophy, male pattern baldness, sexual precociousness, common acne, seborrhea and hypertrichosis. For example, it is known that persons who have been castrated and persons suffering from sexual gland failure almost never develop prostate cancer or benign prostatic hypertrophy.

For example, cyproterone acetate, chlormadinone acetate, flutamide, bicalutamide and the like are used as anti-androgen agents, i.e., androgen receptor antagonists. These anti-androgen agents show an effect in many cases such as drug therapy in prostate cancer, and constitute important treatment drugs in this area. Furthermore, it is known that cyproterone acetate suppresses the occurrence of baldness and the progression of acne in teenagers. Furthermore, in females, cyproterone acetate is used in the treatment of androgenization and hair loss. Flutamide and bicalutamide are used as prostate cancer treatment agents.

However, as problems encountered in these anti-androgen agents, it is known that even if the anti-androgen agents are effective, the disease recurs in almost all cases in two to five years, and in such cases, androgen resistance appears.

Furthermore, it has been reported that hydroxyflutamide, which is the active form of flutamide, causes an increase in androgen receptor transcription activity at a concentration of 10 μmol/L. Moreover, the hydroxyflutamide concentration in the blood in prostate cancer patients treated with flutamide is several μmol/L. However, it has been reported that this concentration reaches a concentration at which hydroxyflutamide shows an agonist effect (see Non-patent Document 1).

Furthermore, it has been reported that there is an increase in the weight of the prostate gland when cyproterone acetate and chlormadinone acetate are continuously administered to castrated rats for two weeks (see Non-patent Document 2). Moreover, in regard to flutamide and bicalutamide, there are also reports of side effects such as liver toxicity and the like. Accordingly, there is a demand for an anti-androgen agent which has a sufficient antagonistic effect, and in which these problems have been solved.

Meanwhile, the compounds represented by the following formula described in Japanese Patent Application No. 4-308579 A (Patent Document 1) and the corresponding European Patent Application No 494819 A (Patent Document 2) are known as phenylimidazolidines that show anti-androgen activity.

[Formula 1]

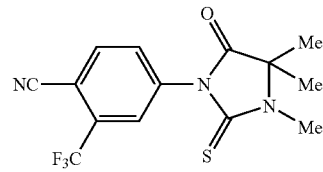

Furthermore, the compounds represented by the following formula described in Japanese Patent Application No. 10-510845 A (Patent Document 3) and the corresponding International Patent Publication WO 97/00071 (Patent Document 4) are known as substituted phenylimidazolidines that show anti-androgen activity.

[Formula 2]

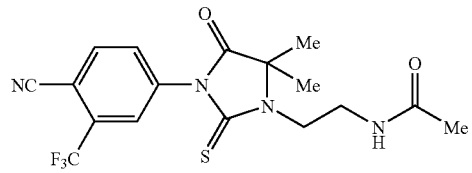

However, the compounds likewise do not constitute means for solving the problems of existing anti-androgen agents.

[Patent Document 1]
  Japanese Patent Application No. 4-308579 A

[Patent Document 2]
  European Patent Application No 494819 A

[Patent Document 3]
  Japanese Patent Application No. 10-510845 A

[Patent Document 4]
  International Patent Publication WO 97/00071

[Non-Patent Document 1]
  J. Biol. Chem., Vol. 270, pp. 19998-20003, 1995

[Non-Patent Document 2]
  Journal of the Endocrine Society of Japan, Vol. 66, pp. 597-606, 1990

DISCLOSURE OF THE INVENTION

Problems to be Solved

It is one object of the present invention to provide imidazolidine derivatives which have a substituted alkyl group in 3-position, and which show a useful activity as drugs, especially an anti-androgen activity, and salts, prodrugs or solvates thereof.

It is another object of the present invention to provide drugs containing the abovementioned imidazolidine derivatives.

Means for Solving the Problems

The present inventors conducted diligent research with the aim of solving the abovementioned problems. As a result of this research, the inventors found that imidazolidine derivatives having a sulfonamide group represented by Formula (I) show anti-androgen activity, and show no or almost no agonist activity, and then completed the present invention.

Specifically, the present invention provides a compound represented by formula (I):

[Formula 3]

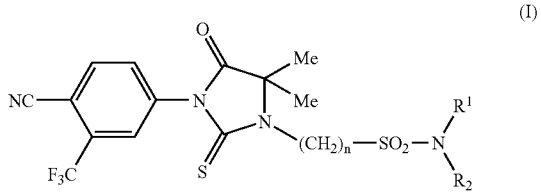

wherein n is an integer selected from 1 to 20, and $R^1$ and $R^2$, which may be the same or different, each represent a hydrogen atom or a linear or branched $C_1$-$C_6$ alkyl group, or a salt, a prodrug or a solvate thereof. Also, the present invention provides a compound represented by formula (I) wherein n is an integer selected from 1 to 10, or a salt, a prodrug or a solvate thereof. Also, the present invention provides a compound represented by formula (I) wherein $R^1$ and $R^2$ are each a hydrogen atom, or a salt, a prodrug or a solvate thereof. Also, the present invention provides a compound represented by formula (I) wherein at least one of $R^1$ and $R^2$ is a methyl group, or a salt, a prodrug or a solvate thereof. Further, the present invention provides a compound represented by formula (I), which is selected from the group consisting of:

4-[3'-(3"-aminosulfonylpropyl)-4',4'-dimethyl-5'-oxo-2'-thioxo-1'-imidazolidinyl]-2-trifluoromethylbenzonitrile;

4-[3'-(4"-aminosulfonylbutyl)-4',4'-dimethyl-5'-oxo-2'-thioxo-1'-imidazolidinyl]-2-trifluoromethylbenzonitrile;

4-[3'-(6"-aminosulfonylhexyl)-4',4'-dimethyl-5'-oxo-2'-thioxo-1'-imidazolidinyl]-2-trifluoromethylbenzonitrile;

4-[3'-(7"-aminosulfonylheptyl)-4',4'-dimethyl-5'-oxo-2'-thioxo-1'-imidazolidinyl]-2-trifluoromethylbenzonitrile;

4-[3'-(8"-aminosulfonyloctyl)-4',4'-dimethyl-5'-oxo-2'-thioxo-1'-imidazolidinyl]-2-trifluoromethylbenzonitrile;

4-[3'-(9"-aminosulfonylnonyl)-4',4'-dimethyl-5'-oxo-2'-thioxo-1'-imidazolidinyl]-2-trifluoromethylbenzonitrile;

4-[3'-(5"-aminosulfonylpentyl)-4',4'-dimethyl-5'-oxo-2'-thioxo-1'-imidazolidinyl]-2-trifluoromethylbenzonitrile;

4-[3'-(4"-N,N-dimethylaminosulfonylbutyl)-4',4'-dimethyl-5'-oxo-2'-thioxo-1'-imidazolidinyl]-2-trifluoromethylbenzonitrile;

4-[3'-(3"-N,N-dimethylaminosulfonylpropyl)-4',4'-dimethyl-5'-oxo-2'-thioxo-1'-imidazolidinyl]-2-trifluoromethylbenzonitrile;

4-[3'-(5"-N,N-dimethylaminosulfonylpentyl)-4',4'-dimethyl-5'-oxo-2'-thioxo-1'-imidazolidinyl]-2-trifluoromethylbenzonitrile;

4-[3'-(6"-N,N-dimethylaminosulfonylhexyl)-4',4'-dimethyl-5'-oxo-2'-thioxo-1'-imidazolidinyl]-2-trifluoromethylbenzonitrile;

4-[3'-(7"-N,N-dimethylaminosulfonylheptyl)-4',4'-dimethyl-5'-oxo-2'-thioxo-1'-imidazolidinyl]-2-trifluoromethylbenzonitrile;

4-[3'-(8"-N,N-dimethylaminosulfonyloctyl)-4',4'-dimethyl-5'-oxo-2'-thioxo-1'-imidazolidinyl]-2-trifluoromethylbenzonitrile;

4-[3'-(9"-N,N-dimethylaminosulfonylnonyl)-4',4'-dimethyl-5'-oxo-2'-thioxo-1'-imidazolidinyl]-2-trifluoromethylbenzonitrile;

4-[3'-(3"-N-methylaminosulfonylpropyl)-4',4'-dimethyl-5'-oxo-2'-thioxo-1'-imidazolidinyl]-2-trifluoromethylbenzonitrile;

4-[3'-(4"-N-methylaminosulfonylbutyl)-4',4'-dimethyl-5'-oxo-2'-thioxo-1'-imidazolidinyl]-2-trifluoromethylbenzonitrile;

4-[3'-(5"-N-methylaminosulfonylpentyl)-4',4'-dimethyl-5'-oxo-2'-thioxo-1'-imidazolidinyl]-2-trifluoromethylbenzonitrile; and 4-[3'-(2"-aminosulfonylethyl)-4',4'-dimethyl-5'-oxo-2'-thioxo-1'-imidazolidinyl]-2-trifluoromethylbenzonitrile or a salt, a prodrug or a solvate thereof.

According to another aspect of the present invention, there provides a drug comprising a compound represented by formula (I) or a salt, a prodrug or a solvate thereof as an active ingredient.

According to still another aspect of the present invention, there provides a pharmaceutical composition comprising a compound represented by formula (I) or a salt, a prodrug or a solvate thereof as an active ingredient. Also, the present invention provides an anti-androgen agent comprising a compound represented by formula (I) or a salt, a prodrug or a solvate thereof as an active ingredient. Also, the present invention provides a prophylactic or therapeutic agent for a disease selected from prostate cancer, benign prostatic hypertrophy, male pattern baldness, sexual precociousness, common acne, seborrhea and hypertrichosis, which comprises a compound represented by formula (I) or a salt, a prodrug or a solvate thereof as an active ingredient.

According to still another aspect of the present invention, there provides the use of a compound represented by formula (I) or a salt, a prodrug or a solvate thereof in manufacturing a medicament that acts as an androgen receptor antagonist.

According to still another aspect of the present invention, there provides a process for preparing a compound represented by formula (I), which comprises the steps of:

reacting a compound represented by formula (II):

[Formula 4]

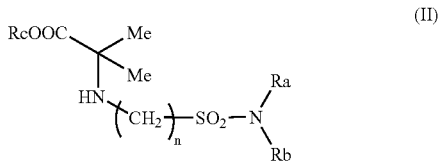

wherein n is an integer selected from 1 to 20;

Ra and Rb, which may be the same or different, are each selected from the group consisting of a linear or branched $C_1$-$C_6$ alkyl group substituted with one or more $W^1$, a linear or branched $C_1$-$C_6$ alkylcarbonyl group which may be substituted with one or more $W^1$, an arylcarbonyl group which may be substituted with one or more $W^2$, a linear or branched $C_1$-$C_6$ alkoxycarbonyl group which may be substituted with one or more $W^1$, an aryloxycarbonyl group which may be substituted with one or more $W^2$, a linear or branched $C_1$-$C_6$ alkylaminocarbonyl group which may be substituted with one or more $W^1$, a linear or branched $C_1$-$C_6$ dialkylaminocarbonyl group which may be substituted with one or more $W^1$, a linear or branched $C_1$-$C_6$ alkylsulfonyl group which may be substituted with one or more $W^1$, an arylsulfonyl group which may be substituted with one or more $W^2$, and $R^1$ and $R^2$;

or

Ra and Rb may be joined together to form a group =CH—$W^3$;

$W^1$ is a linear or branched $C_1$-$C_6$ alkoxy group, a linear or branched $C_1$-$C_6$ alkylthio group, a linear or branched $C_1$-$C_6$ alkylsulfinyl group, a linear or branched $C_1$-$C_6$ alkylsulfonyl group, an aryl group which may be substituted with one or more $W^2$, an aryloxy group which may be substituted with one or more $W^2$, or a $C_1$-$C_3$ aralkyloxy group which may be substituted with one or more $W^2$;

$W^2$ is a linear or branched $C_1$-$C_6$ alkyl group, a linear or branched $C_1$-$C_6$ alkoxy group, a linear or branched $C_1$-$C_6$ haloalkyl group, a halogen atom, a cyano group, or a nitro group;

$W^3$ is a linear or branched $C_1$-$C_6$ alkyl group, a linear or branched $C_1$-$C_6$ alkoxy group, a linear or branched $C_1$-$C_6$ alkylamino group, or a linear or branched $C_1$-$C_6$ dialkylamino group;

$R^1$ and $R^2$ are as defined above; and

Rc is a linear or branched $C_1$-$C_6$ alkyl group with 4-cyano-3-trifluoromethylphenyl isothiocyanate to obtain a compound represented by formula (III):

[Formula 5]

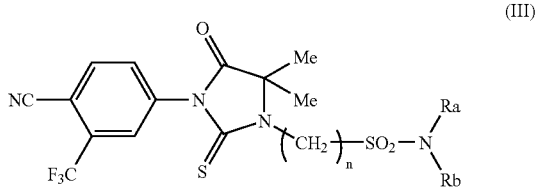

(III)

wherein n, Ra and Rb are as defined above; and a deprotection in cases where at least one of the groups Ra and Rb is other than $R^1$ and $R^2$.

According to still another aspect of the present invention, there also provides, as a synthetic intermediate for a compound represented by formula (I), a compound represented by formula (II):

[Formula 6]

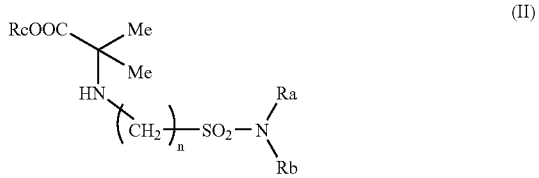

(II)

wherein n, Ra, Rb and Rc are as defined herein above] and a compound represented by formula (III):

[Formula 7]

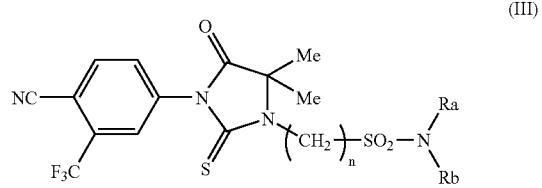

(III)

wherein n, Ra and Rb are as defined herein above, or a salt, a prodrug or a solvate thereof.

According to still another aspect of the present invention, there provides a method for preventing or treating a disease, which comprises administering a compound represented by formula (I) or a salt, a prodrug or a solvate thereof.

EFFECT OF THE INVENTION

The present invention makes it possible to provide imidazolidine derivatives that can be an antiandrogen that shows no occurrence of androgen resistance as a result of long-term administration, and/or side effects such as liver toxicity or the like.

PREFERRED MODE FOR CARRYING OUT
THE INVENTION

In the present invention, the following terms includes the meanings described below unless specifically noted otherwise.

Examples of a linear or branched $C_1$-$C_6$ alkyl group include methyl group, ethyl group, n-propyl group, i-propyl group, n-butyl group, s-butyl group, i-butyl group, t-butyl group, n-pentyl group, 3-methylbutyl group, 2-methylbutyl group, 1-methylbutyl group, 1-ethylpropyl group, n-hexyl group and the like. A linear or branched alkyl group with 1 to 3 carbon atoms is preferable, and methyl group is more preferable, as $R^1$ or $R^2$ in formula (I) of the present invention.

A linear or branched $C_1$-$C_6$ alkoxy group is a group that has the already-defined alkyl group as alkyl moieties. Examples include methoxy group, ethoxy group, n-propoxy group, i-propoxy group, n-butoxy group, s-butoxy group, i-butoxy group, t-butoxy group, n-pentoxy group, 3-methylbutoxy group, 2-methylbutoxy group, 1-methylbutoxy group, 1-ethylpropoxy group, n-hexyloxy group and the like.

A linear or branched $C_1$-$C_6$ alkylcarbonyl group is a group that has the already-defined alkyl group as alkyl moieties. Examples include acetyl group, propionyl group, 2-methylpropionyl group, 2,2-dimethylpropionyl group and the like.

The term aryl group refers to a single-ring or fused-ring arylhydrocarbon group with 6 to 14 carbon atoms. Examples of such a group include phenyl group, 1-naphthyl group, 2-naphthyl group, anthracenyl group and the like. Furthermore, the same is true in cases where an aryl group is included as parts of other substituents.

An aryloxy group is a group that has the already-defined aryl as aryl moieties. Examples include phenoxy group, 1-naphthyloxy group, 2-naphthyloxy group and the like.

Examples of arylcarbonyl group include benzoyl group, 1-naphthoyl group, 2-naphthoyl group and the like.

A linear or branched $C_1$-$C_6$ alkoxycarbonyl group is a group that has the already-defined alkyl group as alkyl moieties. Examples include methoxycarbonyl group, ethoxycarbonyl group, t-butoxycarbonyl group and the like.

Examples of an aryloxycarbonyl group include phenoxycarbonyl group, 1-naphthyloxycarbonyl group, 2-naphthyloxy carbonyl group and the like.

A linear or branched $C_1$-$C_6$ alkylaminocarbonyl group is a group that has the already-defined alkyl group as alkyl moieties. Examples include methylaminocarbonyl group, ethylaminocarbonyl group, t-butylaminocarbonyl group and the like.

A linear or branched $C_1$-$C_6$ dialkylaminocarbonyl group is a group that has the already-defined alkyl group as alkyl moieties. Examples include dimethylaminocarbonyl group, diethylaminocarbonyl group, diisopropylaminocarbonyl group, methyl-t-butylaminocarbonyl group and the like.

A linear or branched $C_1$-$C_6$ alkylthio group is a group that has the already-defined alkyl group as alkyl moieties. Examples include methylthio group, ethylthio group and the like.

A linear or branched $C_1$-$C_6$ alkylsulfinyl group is a group that has the already-defined alkyl group as alkyl moieties. Examples include methylsulfinyl group, ethylsulfinyl group and the like.

A linear or branched $C_1$-$C_6$ alkylsulfonyl group is a group that has the already-defined alkyl group as alkyl moieties. Examples include methanesulfonyl group, ethanesulfonyl group and the like.

Examples of an arylsulfonyl group include benzenesulfonyl group, 1-naphthalenesulfonyl group, 2-naphthalenesulfonyl group and the like.

A linear or branched $C_1$-$C_3$ aralkyl group is a group that has the already-defined alkyl group as a linear or branched alkyl moiety with 1 to 3 carbon atoms. Examples include benzyl group, 1-phenethyl group, 2-phenethyl group and the like.

A linear or branched $C_1$-$C_3$ aralkyloxy group is a group that has the already-defined aralkyl group as a linear or branched aralkyl moiety with 1 to 3 carbon atoms. Examples include benzyloxy group, 1-phenethyloxy group, 2-phenethyloxy group and the like.

Halogen atoms refer to fluorine atoms, chlorine atoms, bromine atoms, iodine atoms and the like.

A linear or branched $C_1$-$C_3$ haloalkyl group is an alkyl group substituted with one or more of the halogen atoms defined above, which has the already-defined alkyl group as a linear or branched alkyl moiety with 1 to 3 carbon atoms. Examples of such a haloalkyl group include fluoromethyl group, chloromethyl group, bromomethyl group, difluoromethyl group, trifluoromethyl group, dichloromethyl group, tirchloromethyl group, chlorodifluoromethyl group, 1,1,1-trifluoroethyl group, 1,1,1-trichloroethyl group, perfluoroethyl group, perfluoropropyl group and the like.

In addition to the abovementioned substituent group, examples of Ra and Rb include a $C_1$-$C_6$ alkoxy $C_1$-$C_6$ alkyl group such as methoxymethyl group, ethoxymethyl group, methoxyethyl group and the like; a $C_1$-$C_3$ aralkyloxy $C_1$-$C_6$ alkyl group such as benzyloxymethyl group and the like; a $C_1$-$C_3$ aralkyl group such as benzyl group, 4-methoxybenzyl group and the like; a $C_1$-$C_3$ aralkyloxycarbonyl group such as benzyloxycarbonyl group and the like; p-toluenesulfonyl group, and the like.

Examples of the abovementioned group =CH—$W^3$ include the group =CH—$CH_3$, the group =CH—$N(CH_3)_2$, the group =CH—$N(CH_2CH_3)_2$, the group =CH—$OCH_3$, the group =CH—$OCH_2CH_3$ and the like. These groups may be cis forms, trans forms or a mixture thereof.

Preferably, n is 1, 2, 3, 4, 5, 6, 7, 8, 9 or 10, more preferably 2 to 9, and even more preferably 2 to 6. Furthermore, in cases where n is 3 or 4, a significant separation of agonist activity and antagonist activity is recognized.

There are no particular restrictions on the deprotection process. However, examples of such processes include hydrolysis reactions performed in the presence of an acid or base, reduction reactions including hydrogenation using Pd/C or the like, dehydrogenation reactions using dichlorodicyanoquinone or the like, and other such reactions.

$R^1$ and $R^2$ may be the same or different, and these groups are preferably a hydrogen atom or a linear or branched alkyl group with 1 to 3 carbon atoms.

Salts of the compounds represented by formula (I) are pharmaceutically acceptable salts which are manufactured by contacting the abovementioned compounds with acids or bases that can be used in the manufacture of drugs. Examples of such salts include hydrochloric acid salts, hydrobromic acid salts, hydroiodic acid salts, sulfuric acid salts, sulfonic acid salts, phosphoric acid salts, phosphonic acid salts; carboxylic acid salts such as acetic acid salts, citric acid salts, malic acid salts, salicylic acid salts and the like; alkali metal salts such as sodium salts, potassium salts and the like; alkaline earth metal salts such as magnesium salts, calcium salts and the like; ammonium salts such as ammonium salts, alkylammonium salts, dialkylammonium salts, trialkylammonium salts, tetraalkylammonium salts and the like, and other such salts.

The term "a prodrug of a compound represented by formula (I)" includes a chemically modified compound that is designed to produce a compound represented by formula (I) in the body after being administered as drugs, by chemical reactions that take place in the body. Examples of such a prodrug include a compound obtained by subjecting a compound represented by formula (I) to a $C_1$-$C_6$ alkylcarbonyl conversion, $C_6$-$C_{10}$ arylcarbonyl conversion, $C_1$-$C_6$ alkoxycarbonyl conversion, $C_1$-$C_6$ alkylaminocarbonyl conversion, $C_1$-$C_6$ alkylsulfonyl conversion or the like, and a compound subjected to an imino conversion using a reagent such as N,N-dimethylformamide dimethylacetal or the like. Specific examples of a prodrug also include the compound represented by formula (III).

A solvate of a compound represented by formula (I) include a compound in which a molecule of a solvent that can be used in the manufacture of drugs is coordinated with the abovementioned compound. For example, such a solvate include a hydrate.

The compound of the present invention represented by general formula (I) is expected to act as anti-androgen agents that do not show any appearance of androgen resistance due to long-term administration, and/or side effects such as toxicity or the like, and are expected to be useful as therapeutic agents for the treatment of diseases such as prostate cancer, benign prostatic hypertrophy, male pattern baldness, sexual precociousness, common acne, seborrhea and hypertrichosis. Furthermore, if the compounds of the present invention represented by general formula (I) are administered beforehand, it is expected that the onset of diseases such as prostate cancer, benign prostatic hypertrophy, male pattern baldness, sexual precociousness, common acne, seborrhea and hypertrichosis will be prevented or delayed. Accordingly, it is expected that these compounds will also constitute prophylactic agents for such diseases.

The pharmaceutical composition of the present invention contains a compound represented by formula (I), or a salt, a prodrug or a solvate thereof, in amounts that is effective in treatment, and a pharmaceutically acceptable carrier. If necessary, this composition may contain other chemotherapeutic agents. For example, one or more agents selected from cell division inhibiting agents, alkylating agents, metabolism inhibiting agents, intercalating antibiotics, growth factor inhibiting agents, cell period inhibiting agents, enzymes, enzyme inhibitors, aromatase inhibitors, topoisomerase inhibitors, biological response modifiers, anti-hormone agents, anti-estrogen agents and anti-androgen agents.

The compound of the present invention represented by general formula (I) is expected to act as anti-androgen agents that do not show any appearance of androgen resistance due to long-term administration, and/or side effects such as toxicity or the like, and are expected to be useful as therapeutic agents for the treatment of diseases such as prostate cancer, benign prostatic hypertrophy, male pattern baldness, sexual precociousness, common acne, seborrhea and hypertrichosis. Furthermore, if the compounds of the present invention represented by general formula (I) are administered beforehand, it is expected that the onset of diseases such as prostate cancer, benign prostatic hypertrophy, male pattern baldness, sexual precociousness, common acne, seborrhea and hypertrichosis will be prevented or delayed. Accordingly, it is expected that these compounds will also constitute prophylactic agents for such diseases.

The compound of the present invention represented by general formula (I), as well as a salt, a prodrug and a solvate thereof, can be administered orally or parenterally in the form of pharmaceutical compositions which also contain pharmaceutically acceptable additive agents such as carriers, excipients, binders, diluents, stabilizing agents, lubricants, flavoring agents, disintegrating agents, coating agents, coloring agents, antioxidants, buffering agents, aqueous solvents, oily solvents, isotonic agents, dispersing agents, preservatives, solubilizing agents, fluidizing agents, analgesic agents, pH adjusting agents, antiseptic agents, base agents and the like. Examples of the abovementioned pharmaceutical composition include granular agents, powder-form agents, tablets, hard capsule agents, soft capsule agents, syrup agents, emulsions, suspensions and the like as orally administered agents. Examples of parenteral agents include injection agents such as subcutaneous injection agents, intravenous injection agents, intramuscular injection agents, intra-abdominal injection agents and the like; transdermal administration agents such as ointments, crèmes, lotions and the like; suppositories such as rectal suppositories, vaginal suppositories and the like; nasal administration formulations; and other agents. These formulations can be manufactured by universally known methods that are commonly used in formulation processes.

Examples of excipients that can be used in the present invention include sugars such as lactose, white sugar, glucose, D-mannitol, sorbit and the like; cellulose and cellulose derivatives such as crystalline cellulose, hydroxypropylcellulose, hydroxypropylmethyl cellulose, methylcellulose and the like; starch and starch derivatives such as corn starch, potato starch, α-starch, dextrin, β-cyclodextrin, carboxymethylstarch sodium, hydroxypropylstarch and the like; silicates such as synthetic aluminum silicate, magnesium aluminum silicate, calcium silicate, magnesium silicate and the like; phosphates such as calcium phosphate and the like; carbonates such as calcium carbonate and the like; sulfates such as calcium sulfate and the like; tartaric acid, potassium hydrogentartarate, magnesium hydroxide and the like.

Examples of binders that can be used include agar, stearyl alcohol, gelatin, traganth, polyvinyl alcohols, polyvinylpyrrolidones; cellulose and cellulose derivatives such as crystalline cellulose, hydroxypropylcellulose, hydroxypropylmethyl cellulose, methylcellulose and the like; starch and starch derivatives such as corn starch, potato starch, α-starch, dextrin, β-cyclodextrin, carboxymethylstarch sodium, hydroxypropylstarch and the like; sugars such as lactose, white sugar, glucose, D-mannitol, sorbit and the like; and other binders.

Examples of stabilizing agents that can be used include hardened oils, sesame oil, sodium chondroitin sulfate, dibutylhydroxytoluene, adipic acid, ascorbic acid, L-ascorbic acid stearic acid esters, sodium L-ascorbate, L-aspartic acid, sodium L-aspartate, acetyltryptophan sodium, acetanalid, aprotinin liquid, aminoethysulfonic acid, aminoacetic acid, DL-alanine, L-alanine; para-oxybenzoic acid esters such as methylparaben, propylparaben and the like; alcohols such as chlorobutanol, benzyl alcohol, phenyl ethyl alcohol and the like; benzalkonium chloride; phenols such as phenol, cresol and the like; sorbic acid; sulfites such as sodium hydrogensulfite, sodium sulfite and the like; edetates such as sodium edentate, tetrasodium edentate and the like; and other stabilizing agents.

Examples of lubricants that can be used include powdered gum Arabic, cacao butter, carmellose calcium, carmellose sodium, caropeptide, hydrated silicon dioxide, hydrated amorphous silicon oxide, dry aluminum hydroxide gel, glycerol, light liquid paraffin, crystalline cellulose, hardened oils, synthetic aluminum silicate, sesame oil, wheat starch, talc, macrogols, phosphoric acid; stearic acids such as stearic acid, calcium stearate, magnesium stearate and the like; waxes such as bleached beeswax, carnauba wax and the like; sulfates such as sodium sulfate and the like; silicates such as magnesium silicate, light amorphous silicic acid and the like; laurylsulfates such as sodium laurylsulfate and the like; and other lubricants.

Examples of flavoring agents that can be used include ascorbic acid, L-aspartic acid, sodium L-aspartate, magnesium L-aspartate, aspartame, hydrangea tea, hydrangea tea extract, powdered hydrangea tea; aminoethylsulfonic acid, aminoacetic acid, DL-alanine, saccharine sodium, dl-menthol, 1-menthols; sugars such as lactose, white sugar, glucose, D-mannitol and the like; and other taste enhancing agents.

Examples of disintegrating agents that can be used include agar, gelatin, traganth, adipic acid, alginic acid, sodium alginate; cellulose and cellulose derivatives such as crystalline cellulose, hydroxypropylcellulose, hydroxypropylmethyl cellulose, methylcellulose and the like; carbonates such as calcium carbonate, sodium hydrogencarbonate, magnesium carbonate and the like; starch and starch derivatives such as corn starch, potato starch, α-starch, dextrin, β-cyclodextrin, carboxymethylstarch sodium, hydroxypropylstarch and the like; and other agents.

Examples of coating agents that can be used include shellac, polyvinylpyrrolidiones, polyethylene glycols, macrogols, methacrylic acid copolymers, liquid paraffin, Eudragit; cellulose derivatives such as cellulose acetate, hydroxypropylcellulose, cellulose acetophthalate, hydroxypropylmethylcellulose and the like; and other coating agents.

Examples of coloring agents that can be used include indigo carmine, caramel, riboflavin and the like.

Examples of buffering agents that can be used include aminoacetic acid, L-arginine, benzoic acid, sodium benzoate, ammonium chloride, potassium chloride, sodium chloride, dry sodium sulfite, dry sodium carbonate, dilute hydrochloric acid, citric acid, calcium citrate, sodium citrate, disodium citrate, calcium gluconate, L-glutamic acid, sodium L-glutamate, creatinine, chlorobutanol, crystalline sodium dihydrogenphosphate, disodium succinate, acetic acid, potassium acetate, sodium acetate, tartaric acid, sodium hydrogencarbonate, sodium carbonate, triethanolamine, lactic acid, sodium lactate liquid, glacial acetic acid, boric acid, maleic acid, citric anhydride, anhydrous sodium citrate, anhydrous sodium acetate, anhydrous sodium carbonate, anhydrous sodium monohydrogenphosphate, anhydrous trisodium phosphate, anhydrous sodium dihydrogenphosphate, dl-malic acid, phosphoric acid, trisodium phosphate, sodium hydrogenphosphate, dipotassium phosphate, potassium dihydrogenphosphate, sodium dihydrogenphosphate, sodium dihydrogenphosphate monohydrate and the like.

Examples of aqueous solvents that can be used include distilled water, physiological saline, Ringer's solution and the like.

Examples of oily solvents that can be used include propylene glycol; vegetable oils such as olive oil, sesame oil, cottonseed oil, corn oil and the like; and other agents.

Examples of isotonic agents that can be used include potassium chloride, sodium chloride, glycerol, sodium bromide, D-sorbitol, nicotinic acid amide, glucose, boric acid and the like.

Examples of dispersing agents that can be used include gum arabic, alginic acid propylene glycol ester, sorbitan sesquieoleate, D-sorbitol, traganth, methylcellulose, aluminum monostearate, aminoalkyl methacrylate copolymer RS, lactose, concentrated glycerol, propylene glycol, macrogols, sodium laurylsulfate; stearic acid and salts thereof such as calcium stearate, lead stearate, magnesium stearate and the like; and other dispersing agents.

Examples of preservatives that can be used include benzalkonium chloride, benzethonium chloride, dry sodium sulfite, dry sodium sulfate, cresol, chlorocresol, dibutylhydroxytoluene, potassium sorbate, sodium dehydroacetate, phenol, formalin, phosphoric acid, gum benzoin, thymerosal, thymol, sodium dehydroacetate; alcohols such as chlorobutanol, phenethyl alcohol, propylene glycol, benzyl alcohol and the like; para-oxybenzoic acid esters such as isobutyl para-oxybenzoate, ethyl para-oxybenzoate, methyl para-oxybenzoate and the like; and other preservatives.

Examples of solubilizing agents that can be used include sodium benzoate, ethylenediamine, citric acid, sodium citrate, glycerol, sodium acetate, sodium salicylate, sorbitan sesquioleate, nicotinic acid amide, glucose, benzyl alcohol, polyvinylpyrrolidones, acetone, ethanol, isopropanol, D-sorbitol, sodium hydrogencarbonate, sodium carbonate, lactose, urea, white sugar and the like.

Examples of fluidizing agents that can be used include hydrated silicon dioxide, talc, anhydrous ethanol, crystalline cellulose, synthetic aluminum silicate, calcium hydrogenphosphate; stearic acid and salts of the same such as magnesium stearate and the like; and other agents.

Examples of analgesic agents that can be used include benzalkonium chloride, caproin hydrochloride, meprylcaine hydrochloride, lidocaine hydrochloride, lidocaine and the like.

Examples of pH adjusting agents that can be used include hydrochloric acid, citric acid, succinic acid, acetic acid, boric acid, maleic acid, sodium hydroxide and the like.

Examples of antiseptic agents that can be used include benzoic acid, sodium benzoate, cetylpyridinium chloride, salicylic acid, sodium salicylate, sorbic acid, potassium sorbate, thymol, methyl para-oxybenzoate, butyl para-oxybenzoate and the like.

Examples of base agents that can be used include glycerol, stearyl alcohol, polyethylene glycols, propylene glycol, cetanol, lard, white Vaseline, paraffin, bentonite, lanoline fatty acid isopropyl ester, Vaseline, polysorbates, macrogols, lauryl alcohol, sodium laurylsulfate, ethyl linolate, sodium hydrogenphosphate, rosin; vegetable oils such as olive oil, sesame oil, wheat germ oil and the like; and other base agents.

The amount of compounds represented by general formula (I) in the pharmaceutical composition of the present invention varies according to the agent type, but is preferably approximately 0.1 to 100 wt % based on the total amount of the pharmaceutical composition. Furthermore, the amount of the pharmaceutical composition of the present invention that is administered may vary over a wide range depending on the subject of administration (warm-blooded animals such as humans), seriousness of the disease, age, sex, administration method, physician's diagnosis and the like. However, in regard to the amount of compounds represented by formula (I) administered to adults, it is preferable that this amount be approximately 0.1 to 500 mg/kg per day both in the case of oral administration and in the case of parenteral administration. Furthermore, the abovementioned administration amount is the value per unit weight of the object of administration. Furthermore, in the present invention, depending on the seriousness of the disease, judgment of the physician and the like, the abovementioned administration amount may be administered as one dose in a period ranging from one day to one month, or may be divided into several doses or more.

[General Procedures for Synthesis]

The compounds of the present invention represented by general formula (I) can be manufactured, e.g., according to the following methods A to D with or without modifications depending on the compounds to be manufactured.

[Formula 8-1]

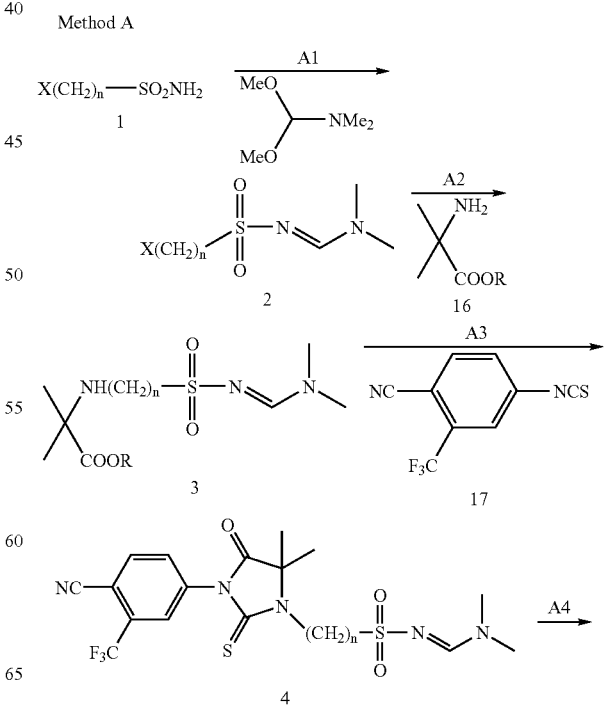

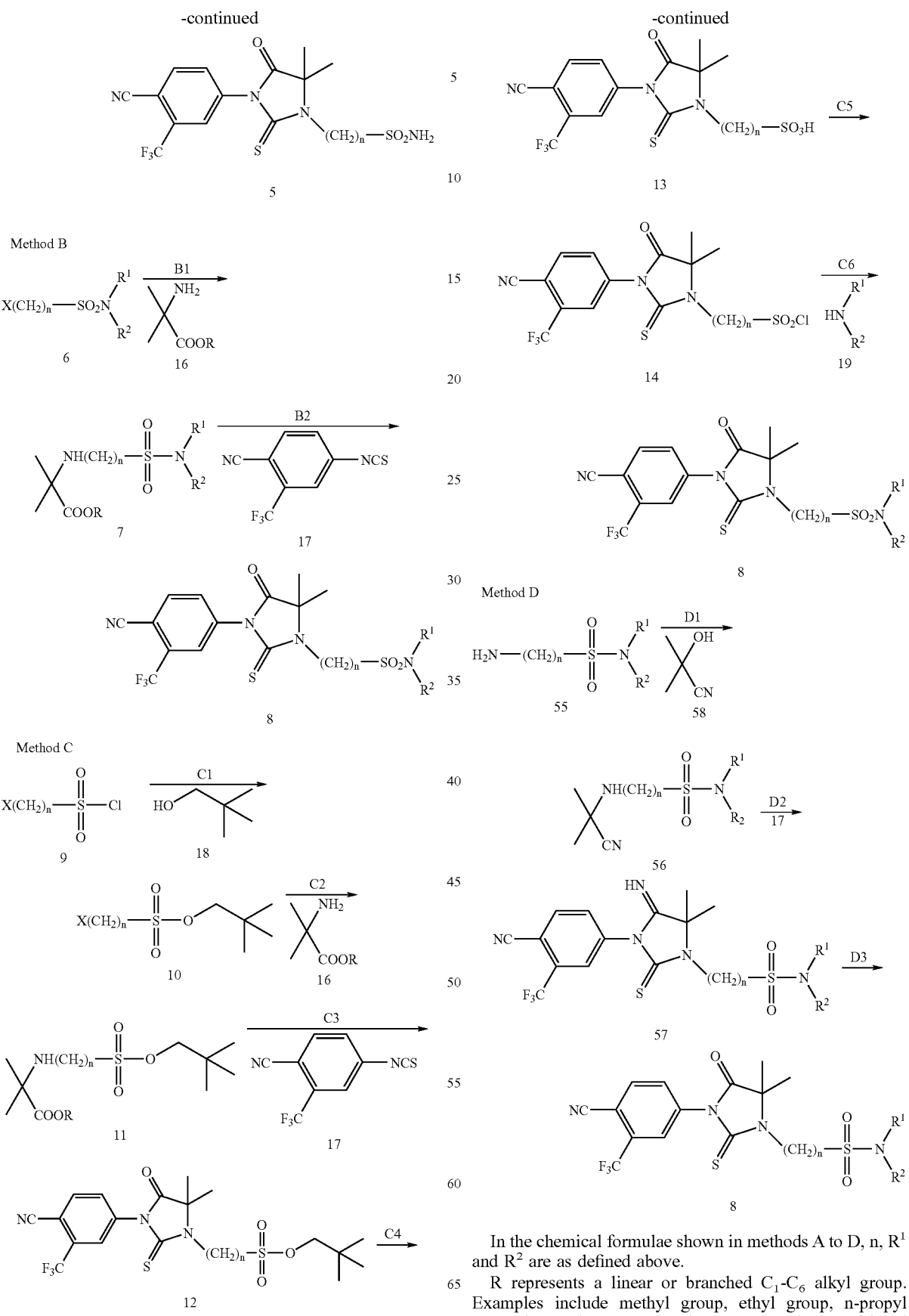
In the chemical formulae shown in methods A to D, n, $R^1$ and $R^2$ are as defined above.
R represents a linear or branched $C_1$-$C_6$ alkyl group. Examples include methyl group, ethyl group, n-propyl group, i-propyl group, n-butyl group, s-butyl group, i-butyl group, t-butyl group, n-pentyl group, 3-methylbutyl group, 2-methylbutyl group, 1-methylbutyl group, 1-ethylpropyl group, n-hexyl group and the like. Preferred is a linear or branched $C_1$-$C_3$ alkyl group, and more preferred are methyl group and ethyl group.

X represents a leaving group such as a halogen atom (e.g., a chlorine atom, a bromine atom, an iodine atom), methanesulfonyloxy group, p-toluenesulfonyloxy group or the like. Preferred is a halogen atom such as a chlorine atom, a bromine atom, an iodine atom or the like.

Method A is a method for preparing compound 5, in which both $R^1$ and $R^2$ are a hydrogen atom among the compounds represented by general formula (I).

Step A1 is a step in which compound 2 is manufactured; this compound is manufactured by reacting compound 1 and compound 15 in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene; quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are dimethylsulfoxide, dimethylacetamide, dimethylimidazolidinone, dimethylformamide, N-methylpyrrolidone, acetonitrile and the like, and dimethylformamide and the like are especially preferable.

The reaction temperature varies depending on the type of solvent used and the like, but is ordinarily −30° C. to 100° C., and is preferably 0° C. to 50° C.

The reaction time varies depending on the reaction temperature and the like, but is ordinarily 10 minutes to 48 hours, and is preferably 30 minutes to 24 hours.

Step A2 is a step in which compound 3 is manufactured; this is achieved by reacting compound 2 and compound 16 in the presence of a base with or without additives in an inert solvent.

There are no particular restrictions on the inert solvent used, as long as this solvent does not participate in the reaction; examples of such inert solvents include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and also cyclohexane, dimethylsulfoxide, dimethylacetamide, dimethylimidazolidinone, dimethylformamide, N-methylpyrrolidone, acetonitrile and the like. Especially suitable are dimethylsulfoxide, dimethylacetamide, dimethylimidazolidinone, dimethylformamide, N-methylpyrrolidone, acetonitrile and the like. These inert solvents may be used singly or in mixtures.

Examples of bases that can be used include carbonates such as potassium carbonate and sodium carbonate; metal hydrides such as sodium hydride, potassium hydride and calcium hydride; alkyllithium compounds such as methyllithium, ethyllithium, n-butyllithium and t-butyllithium; metal hydroxides such as lithium hydroxide, sodium hydroxide, potassium hydroxide, potassium hydroxide, calcium hydroxide, barium hydroxide and cesium hydroxide; metal amides such as sodium amide, potassium bistrimethylsilylamide, sodium bistrimethylsilylamide and lithium diisoprylamide; amines such as triethylamine, diisopropylethylamine, 1,8-diazabicyclo[5.4.0]-7-undecene, pyridine, dimethylaminopyridine and pyrazine; and other compounds such as sodium tetraborate, sodium iodide, lithium hexamethyldisilazane, sodium hexamethyldisilazane, potassium hexamethyldisilazane and the like. Especially suitable are carbonates such as potassium carbonate and sodium carbonate.

There are no particular restrictions on additives used, as long as these additive accelerate the progress of the reaction; examples of additives that can be used include potassium iodide, sodium iodide, tetra-n-butylammonium iodide and the like.

The reaction temperature varies depending on the type of solvent used and the like, but is ordinarily 0° C. to 150° C., and is preferably 30° C. to 100° C.

The reaction time varies depending on the reaction temperature and the like, but is ordinarily 10 minutes to 48 hours, and is preferably 30 minutes to 24 hours.

Step A3 is a step in which compound 4 is manufactured; this is achieved by reacting compound 3 and compound 17 in the presence of a base or without a base in an inert solvent.

There ate no particular restrictions on the inert solvent used, as long as this solvent does not participate in the reaction. However, examples of such inert solvents include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and also cyclohexane, dimethylsulfoxide, dimethylacetamide, dimethylimidazolidinone, dimethylformamide, N-methylpyrrolidone, acetonitrile and the like. Especially suitable are halogen type solvents such as dichloromethane, chloroform and carbon tetrachloride, and ether type solvents such as diethyl ether, tetrahydrofuran, dioxane and dimethoxyethane, and dichloromethane, tetrahydrofuran and the like are even more preferable.

Examples of bases that can be used include amines such as triethylamine, diisopropylethylamine, 1,8-diazabicyclo [5.4.0]-7-undecene, pyridine, dimetylaminopyridine and pyrazine. Preferably, the base used is triethylamine, dimethylaminopyridine or the like. Such a base may be used or omitted. However, the use of a base is preferable.

The reaction temperature varies depending on the type of solvent used and the like, but is ordinarily −30° C. to 100° C., and is preferably 0° C. to 50° C.

The reaction time varies depending on the reaction temperature and the like, but is ordinarily 10 minutes to 48 hours, and is preferably 30 minutes to 24 hours.

Step A4 is a step in which compound 5 is manufactured; this is achieved by hydrolyzing compound 4 in an inert solvent.

There are no particular restrictions on the inert solvent that is used, as long as this solvent does not participate in the reaction. Examples of solvents that can be used include alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol, and ether type solvents such as diethyl ether, tetrahydrofuran, dioxane and dimethoxyethane; furthermore, dioxane and the like are especially preferable.

There are no particular restrictions on the acid used. However, examples of acids that can be used include hydrochloric acid, sulfuric acid and the like. Here, hydrochloric acid and the like are especially suitable.

The reaction temperature varies depending on the type of solvent used and the like, but is ordinarily 0° C. to 200° C., and is preferably 20° C. to 150° C.

The reaction time varies depending on the reaction temperature and the like, but is ordinarily 10 minutes to 48 hours, and is preferably 30 minutes to 24 hours.

Method B is a method for manufacturing compound 8, which is a compound represented by general formula (I) in which $R^1$ and $R^2$ may be the same or different, and are a hydrogen atom or a linear or branched $C_1$-$C_6$ alkyl group.

Step B1 is a step for manufacturing compound 7; this is accomplished by reacting compound 6 and compound 16 in the presence of a base, with or without additive, in an inert solvent, and is performed in the same manner as step A2 of method A.

Step B2 is a step for manufacturing compound 8; this is accomplished by reacting compound 7 and compound 17 in the presence of a base or without a base in an inert solvent, and is performed in the same manner as step A3 of method A.

Method C is another method for manufacturing compound 8, which is a compound represented by general formula (I) in which $R^1$ and $R^2$ may be the same or different, and are a hydrogen atom or a linear or branched $C_1$-$C_6$ alkyl group.

Step C1 is a step for manufacturing compound 10; this is accomplished by reacting compound 9 and compound 18 in the presence of a base in an inert solvent. The alcohol used in this step may be a linear or branched alkyl alcohol with 1 to 6 carbon atoms, or a linear or branched aralkyl alcohol with 1 to 3 carbon atoms or aryl alcohol. For example, methanol, ethanol, n-propanol, isopropanol, t-butanol, neopentyl alcohol (compound 18), benzyl alcohol or the like may be used.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane; and dichloromethane and the like are especially preferable.

Examples of bases that can be used include amines such as triethylamine, diisopropylethylamine, 1,8-diazabicyclo[5.4.0]-7-undecene, pyridine, dimethylaminopyridine and pyrazine. Preferably, the base used is triethylamine, dimethylaminopyridine or the like.

The reaction temperature varies depending on the type of solvent used and the like, but is ordinarily −30° C. to 100° C., and is preferably −10° C. to 30° C.

The reaction time varies depending on the reaction temperature and the like, but is ordinarily 10 minutes to 48 hours, and is preferably 30 minutes to 24 hours.

Step C2 is a step for manufacturing compound 11; this is accomplished by reacting compound 10 and compound 16 in the presence of a base, with or without additives, in an inert solvent. This step is performed in the same manner as step A2 of method A.

Step C3 is a step for manufacturing compound 12; this is accomplished by reacting compound 11 and compound 17 in the presence of a base or without a base in an inert solvent. This step is performed in the same manner as step A3 of method A.

Step C4 is a step for manufacturing compound 13; this is accomplished by reacting compound 12 with tetramethylammonium chloride or the like in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are dimethylsulfoxide, dimethylacetamide, dimethylimidazolidinone, dimethylformamide, N-methylpyrrolidone, acetonitrile and the like, and dimethylformamide and the like are especially preferable.

The reaction temperature varies depending on the type of solvent used and the like, but is ordinarily 30° C. to 250° C., and is preferably 80° C. to 230° C.

The reaction time varies depending on the reaction temperature and the like, but is ordinarily 10 minutes to 48 hours, and is preferably 30 minutes to 24 hours.

Step C5 is a step for manufacturing compound 14; this is accomplished by reacting a salt formed by compound 13 and a base such as triethylamine or the like with a reagent such as triphenylphosphine—thionyl chloride or the like in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane; and dichloromethane and the like are especially preferable.

The reaction temperature varies depending on the type of solvent used and the like, but is ordinarily −30° C. to 50° C., and is preferably 0° C. to 30° C.

The reaction time varies depending on the reaction temperature and the like, but is ordinarily 10 minutes to 48 hours, and is preferably 30 minutes to 24 hours.

Step C6 is a step for manufacturing compound 8; this is accomplished by reacting compound 14 and compound 19 in an inert solvent.

There are no particular restrictions on the inert solvent that is used, as long as this solvent does not participate in the reaction. Examples of solvents that can be used include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are halogen type solvents such as dichloromethane, chloroform and carbon tetrachloride, and ether type solvents such as diethyl ether, tetrahydrofuran, dioxane and dimethoxyethane; and dichloromethane and the like are especially preferable.

The reaction temperature varies depending on the type of solvent used and the like, but is ordinarily −30° C. to 50° C., and is preferably 0° C. to 30° C.

The reaction time varies depending on the reaction temperature and the like, but is ordinarily 10 minutes to 48 hours, and is preferably 30 minutes to 24 hours.

Method D is another method for manufacturing compound 8, which is a compound represented by general formula (I) in which $R^1$ and $R^2$ may be the same or different, and are a hydrogen atoms or a linear or branched $C_1$-$C_6$ alkyl group.

Step D1 is a step for manufacturing compound 56, and is achieved by reacting compound 55 with compound 58 in the inert solvent.

There are no particular restrictions on the inert solvent that is used, as long as this solvent does not participate in the reaction. Examples of solvents that can be used include ether type solvents such as diethyl ether, tetrahydrofuran, dioxane and dimethoxyethane; alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; and other solvents such as dimethylsulfoxide, dimethylacetamide and the like. Most suitable are methanol, ethanol, diethyl ether and the like, and methanol is especially preferable.

The reaction temperature varies depending on the type of solvent used and the like, but is ordinarily 0° C. to 200° C., and is preferably 10° C. to 100° C.

The reaction time varies depending on the reaction temperature and the like, but is ordinarily 10 minutes to 48 hours, and is preferably 30 minutes to 24 hours.

Step D2 is a step for manufacturing compound 57; this is accomplished by reacting compound 56 and compound 17 in the presence of a base or without a base in an inert solvent.

There are no particular restrictions on the inert solvent used, as long as this solvent does not participate in the reaction. However, examples of such inert solvents include halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and also cyclohexane, dimethylsulfoxide, dimethylacetamide, dimethylimidazolidinone, dimethylformamide, N-methylpyrrolidone, acetonitrile and the like. Especially suitable are halogen type solvents such as dichloromethane, chloroform and carbon tetrachloride, and ether type solvents such as diethyl ether, tetrahydrofuran, dioxane and dimethoxyethane, and dichloromethane, tetrahydrofuran and the like are even more preferable.

Examples of bases that can be used include amines such as triethylamine, diisopropylethylamine, 1,8-diazabicyclo[5.4.0]-7-undecene, pyridine, dimetylaminopyridine and pyrazine. Preferably, the base used is triethylamine, dimethylaminopyridine or the like. Such a base may be used or omitted. However, the use of a base is preferable.

The reaction temperature varies depending on the type of solvent used and the like, but is ordinarily −30° C. to 100° C., and is preferably 0° C. to 50° C.

The reaction time varies depending on the reaction temperature and the like, but is ordinarily 10 minutes to 48 hours, and is preferably 30 minutes to 24 hours.

Step D3 is a step for manufacturing compound 8; this is accomplished by hydrolyzing compound 57 in an inert solvent.

There are no particular restrictions on the inert solvent that is used, as long as this solvent does not participate in the reaction. Examples of solvents that can be used include alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol; halogen type solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline and chlorobenzene; and other solvents such as cyclohexane, dimethylsulfoxide, dimethylacetamide, dimethylimidazolidinone, dimethylformamide, N-methylpyrrolidone, acetonitrile and the like. Most suitable are alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol and 1,5-pentanediol, and ether type solvents such as diethyl ether, tetrahydrofuran, dioxane and dimethoxyethane; furthermore, dioxane and the like are especially preferable.

There are no particular restrictions on the acid used. However, examples of acids that can be used include hydrochloric acid, sulfuric acid and the like. Here, hydrochloric acid and the like are especially preferable.

The reaction temperature varies depending on the type of solvent used and the like, but is ordinarily 0° C. to 200° C., and is preferably 20° C. to 150° C.

The reaction time varies depending on the reaction temperature and the like, but is ordinarily 10 minutes to 48 hours, and is preferably 30 minutes to 24 hours.

In cases where groups requiring protection and deprotection are present in the respective processes of the above-mentioned methods A through D, these respective groups can be subjected to protection and deprotection by method that are universally known to persons skilled in the art. For example, in such protection and deprotection, reference may be made to "Protective Groups in Organic Synthesis $2^{nd}$ Edition", Theodora W. Green, John Wiley & Sons, Inc., 1991 or the like.

The above compound 1, compound 6 and compound 55, which are starting materials, are either universally known, or can easily be manufactured by universally known methods or methods similar to such universally known methods [see, e.g., The Journal of Organic Chemistry, 52(11), 2162-2166 (1987); The Journal of Organic Chemistry, 58(5), 1128-1135 (1993); Bioorganic & Medicinal Chemistry Letters, 8(13), 1607-1612 (1998)].

The abovementioned compound 9, compound 15, compound 16, compound 18 and compound 19, which are starting materials, are easily obtainable as commercially marketed products, or else are universally known or can easily be manufactured by universally known methods or methods similar to these universally known methods. Furthermore, compound 16 used in the present invention may be a salt such as a hydrochloride or the like. Hydrochloride salts are suitable for use.

The above compound 17, which is a starting material, is universally known and can easily be manufactured by universally known methods or methods similar to such universally known methods [see, e.g., The Journal of Steroid Biochemistry and Molecular Biology, 48(1), 111-119 (1994)].

EXAMPLES

Preferred examples of the present invention will be described in detail below. However, the present invention is not limited to these examples.

NMR was measured using a nuclear magnetic resonance apparatus ARX 300 (manufactured by Bruker). Furthermore, mass analysis was performed using a mass analysis apparatus Q-micro, Triple Quadrupole Mass Spectrometer (manufactured by MICROMASS). Furthermore, Rf values in thin-layer chromatography were measured using a silica gel plate Silica gel 60 $F_{254}$ (manufactured by Merck).

Example 1

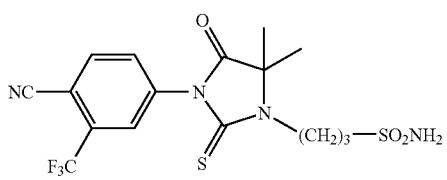

(First Step)

[Formula 10]

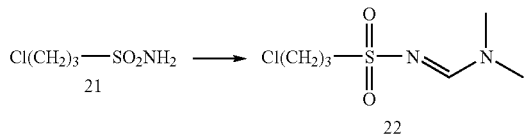

Compound 21 (4.0 g) was dissolved in N,N-dimethylformamide (20 ml). To this solution, N,N-dimethylformamide dimethylacetal (3.7 ml) was added and stirred at room temperature for 1 hour. After addition of ethyl acetate, the organic layer was washed with water and dried over magnesium sulfate. After filtration, the solvent was distilled off under reduced pressure to give the desired compound (compound 22) (3.05 g, yield 57%).

$^1$H-NMR (300 MHz, CDCl$_3$) δ: 2.25-2.34 (2H, m), 3.05 (3H, s), 3.15 (3H, s), 3.18 (2H, t, J=7.2 Hz), 3.71 (2H, t, J=6.0 Hz), 8.05 (1H, s).

Rf value (silica gel plate, developing solvent: ethyl acetate:n-hexane=2:1): 0.31.

(Second Step)

[Formula 11]

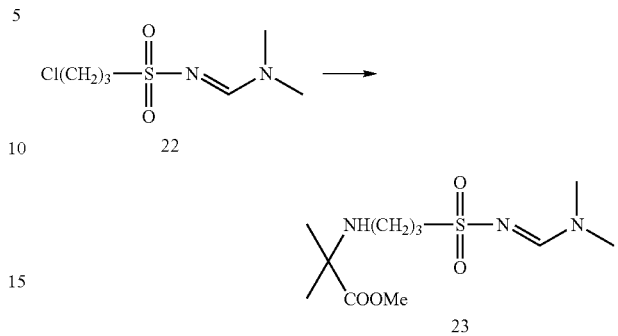

2-Aminoisobutyric acid methyl ester hydrochloride (4.33 g) and potassium carbonate (7.8 g) were dissolved in N,N-dimethylformamide (30 ml) and stirred at room temperature for 30 minutes. To this solution, a solution of compound 22 (3.0 g) in N,N-dimethylformamide (20 ml) and sodium iodide (2.11 g) were added and stirred at 80° C. to 90° C. for 15 hours. After cooling, water was added and the reaction mixture was extracted with ethyl acetate. The organic layer was washed with water and dried over magnesium sulfate. After filtration, the solvent was distilled off under reduced pressure. The resulting residue was purified by silica gel column chromatography (NH silica, developing solvent: ethyl acetate:n-hexane=1:1 to 2:1 to 4:1) to give the desired compound (compound 23) (1.81 g, yield 44%).

$^1$H-NMR (300 MHz, CDCl$_3$) δ: 1.29 (6H, s), 1.89-1.94 (2H, m), 2.57 (2H, t, J=6.8 Hz), 3.04 (3H, s), 3.07-3.11 (2H, m), 3.13 (3H, s), 3.70 (3H, s), 8.03 (1H, s).

Rf value (silica gel plate, developing solvent: ethyl acetate:n-hexane=3:1): 0.09.

(Third Step)

[Formula 12]

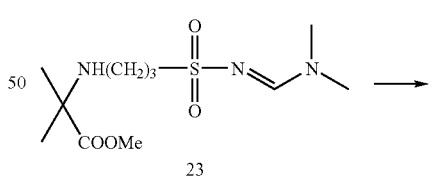

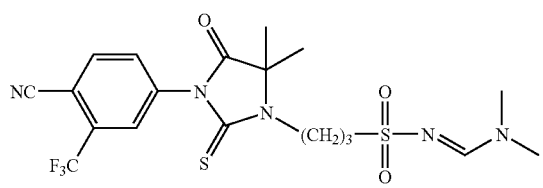

Compound 23 (2.2 g) was dissolved in tetrahydrofuran (34 ml). To this solution, triethylamine (0.21 ml) and 4-cyano-3-trifluoromethylphenyl isothiocyanate (1.71 g) were added and stirred at room temperature for 2 hours. The reaction solution was concentrated and the resulting residue was purified by silica gel column chromatography (NH silica, developing solvent: ethyl acetate:n-hexane=1:1 to 2:1 to 4:1) to give the desired compound (compound 24) (2.6 g, yield 71%).

$^1$H-NMR (300 MHz, CDCl$_3$) δ: 1.62 (6H, s), 2.35-2.42 (2H, m), 3.06 (3H, s), 3.09-3.14 (2H, m), 3.15 (3H, s), 3.92-3.97 (2H, m), 7.77 (1H, dd, J=2.0, 8.2 Hz), 7.90 (1H, d, J=2.0 Hz), 7.95 (1H, d, J=8.2 Hz), 8.07 (1H, s).

Rf value (silica gel plate, developing solvent: ethyl acetate:methanol=3:1): 0.53.

(Fourth Step)

[Formula 13]

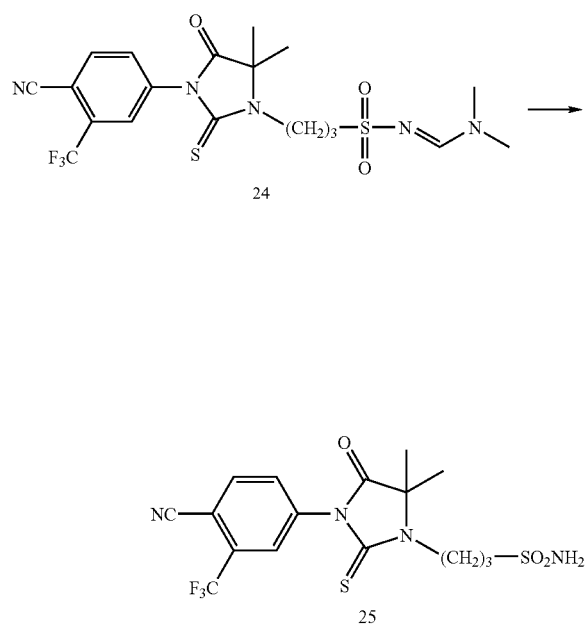

Compound 24 (2.6 g) was dissolved in 1,4-dioxane (25 ml), followed by addition of 6N-hydrochloric acid (25 ml). The resulting mixture was heated under reflux for 1 hour. After cooling, water was added and the reaction mixture was extracted with dichloromethane. The organic layer was washed with water and dried over magnesium sulfate. After filtration and concentration under reduced pressure, the resulting residue was purified by silica gel column chromatography (developing solvent: ethyl acetate:n-hexane=1:1 to 2:1 to 4:1) to give the desired compound (compound 25) (1.62 g, yield 70%).

$^1$H-NMR (300 MHz, CDCl$_3$) δ: 1.62 (6H, s), 2.36-2.46 (2H, m), 3.28 (2H, t, J=7.1 Hz), 3.90-3.95 (2H, m), 4.85 (2H, s), 7.77 (1H, dd, J=2.3, 8.4 Hz), 7.90 (1H, d, J=2.3 Hz), 7.97 (1H, d, J=8.4 Hz).

Rf value (silica gel plate, developing solvent: ethyl acetate): 0.56.

MS(ESI$^-$): 433.3 ([M−H]$^-$).

The following compound was synthesized by the same method as in Example 1.

TABLE 1

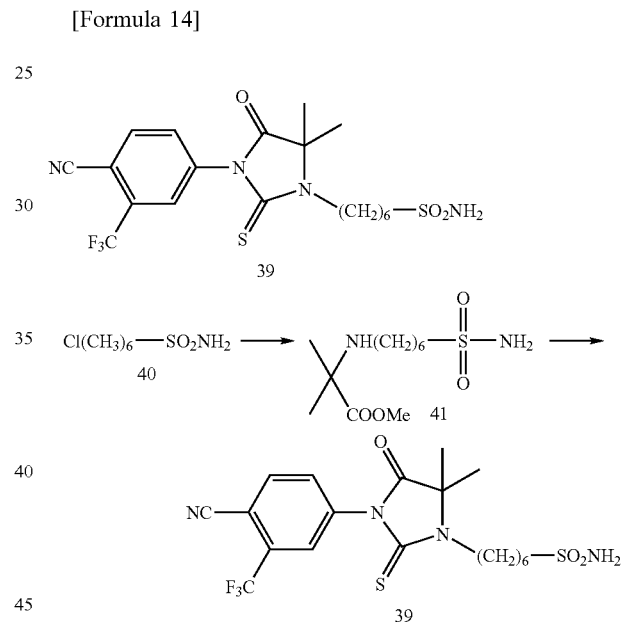

| Example No. | n | Data |
|---|---|---|
| 2 | 4 | Rf: 0.18 (ethyl acetate:n-hexane = 2:1) MS(ESI$^-$): 447.2([M−H]$^-$) |

Example 3

[Formula 14]

2-Aminoisobutyric acid methyl ester hydrochloride (215 mg) and potassium carbonate (406 mg) were dissolved in a mixed solvent of acetonitrile (2 ml) and dimethylformamide (0.4 ml), followed by stirring at room temperature for 1.5 hours. After addition of compound 40 (93 mg) and tetra-n-butylammonium iodide (172 mg), the reaction mixture was heated under reflux for 19 hours. After cooling, water was added and the reaction mixture was extracted with ethyl acetate. The organic layer was washed with brine and dried over magnesium sulfate. After filtration, the solvent was distilled off under reduced pressure to give a crude product of compound 41 (94 mg). 4-Cyano-3-trifluoromethylphenyl isothiocyanate (54 mg) was dissolved in tetrahydrofuran (1 ml). To this solution, the above crude product of compound 41 (94 mg) and triethylamine (0.006 ml) were added and stirred at room temperature for 7.5 hours. The reaction solution was purified by silica gel column chromatography (developing solvent: ethyl acetate:n-hexane=1:1 to 2:1) and reversed-phase column chromatography (packing material: LiChroprep RP-18, developing solvent: methanol:water=2:3 to 1:1) to give the desired compound (compound 39) (12 mg, yield 5.4%).

$^1$H-NMR (300 MHz, CDCl$_3$) δ: 1.43-1.56 (4H, m), 1.61 (6H, s), 1.84-1.93 (4H, m), 3.11-3.16 (2H, m), 3.66-3.71 (2H, m), 4.68 (2H, s), 7.77 (1H, dd, J=1.9, 8.5 Hz), 7.90 (1H, d, J=1.9 Hz), 7.95 (1H, d, J=8.5 Hz).

Rf value (silica gel plate, developing solvent: ethyl acetate:n-hexane=1:1): 0.07.

MS(ESI): 477.5 ([M+H]$^+$).

The following compounds were synthesized by the same method as in Example 3.

TABLE 2

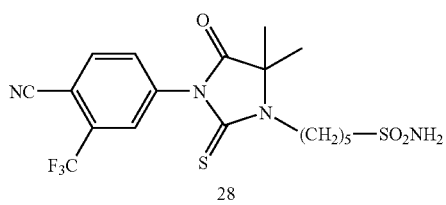

| Example No. | n | Data |
|---|---|---|
| 4 | 7 | MS(ESI): 491.5([M+H]$^+$) |
| 5 | 8 | Rf: 0.20 (n-hexane:ethyl acetate = 1:2) MS(ESI): 505.6([M+H]$^+$) |
| 6 | 9 | Rf: 0.50 (n-hexane:ethyl acetate = 1:2) MS(ESI): 519.4([M+H]$^+$) |

Example 7

[Formula 15]

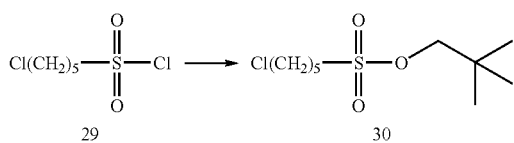

(First Step)

[Formula 16]

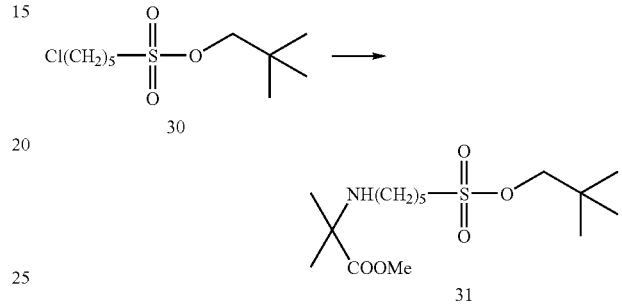

Compound 29 (2.05 g) and neopentyl alcohol (0.96 g) were dissolved in dichloromethane (20 ml) and cooled to 0° C. To this solution, triethylamine (4.6 ml) was added dropwise and stirred at 0° C. to 5° C. for 2.5 hours. The reaction solution was washed with saturated aqueous sodium hydrogencarbonate and the organic layer was dried over magnesium sulfate. After filtration and concentration under reduced pressure, the resulting residue was purified by silica gel column chromatography (developing solvent: ethyl acetate:n-hexane=1:10) to give the desired compound (compound 30) (743 mg, yield 29%).

$^1$H-NMR (300 MHz, CDCl$_3$) δ: 0.99 (9H, s), 1.58-1.67 (2H, m), 1.78-1.96 (4H, m), 3.06-3.16 (2H, m), 3.55 (2H, t, J=6.5 Hz), 3.87 (2H, s).

Rf value (silica gel plate, developing solvent: ethyl acetate:n-hexane=1:9): 0.53.

(Second Step)

[Formula 17]

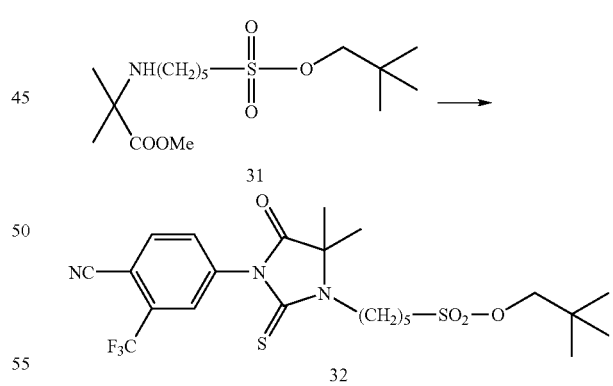

The desired compound (compound 31) (357 mg, yield 37%) was obtained from compound 30 (743 mg) by the same method as in the second step of Example 1.

$^1$H-NMR (300 MHz, CDCl$_3$) δ: 0.99 (9H, s), 1.30 (6H, s), 1.48-1.60 (4H, m), 1.85-1.91 (2H, m), 2.43-2.48 (2H, m), 3.07-3.12 (2H, m), 3.70 (3H, s), 3.86 (2H, s).

Rf value (silica gel plate, developing solvent: ethyl acetate:n-hexane=1:1): 0.35.

(Third Step)

[Formula 18]

The desired compound (compound 32) (465 mg, yield 82%) was obtained from compound 31 (357 mg) by the same method as in the third step of Example 1.

$^1$H-NMR (300 MHz, CDCl$_3$) δ: 0.99 (9H, s), 1.59 (6H, s), 1.50-1.62 (2H, m), 1.87-2.00 (4H, m), 3.15 (2H, t, J=7.6 Hz), 3.67-3.73 (2H, m), 3.88 (2H, s), 7.77 (1H, dd, J=1.6, 8.5 Hz), 7.89 (1H, d, J=1.6 Hz), 7.96 (1H, d, J=8.5 Hz).

Rf value (silica gel plate, developing solvent: ethyl acetate:n-hexane=1:1): 0.40.

(Fourth Step)

[Formula 19]

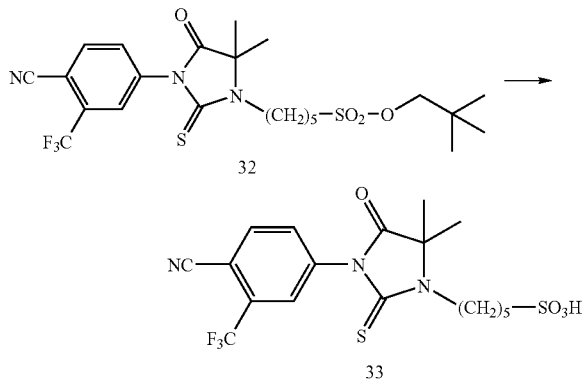

Compound 32 (460 mg) was dissolved in N,N-dimethylformamide, followed by addition of tetramethylammonium chloride (472 mg). The resulting mixture was heated under reflux for 6 hours. After cooling, water was added and the reaction mixture was extracted with dichloromethane. The organic layer was washed with water and brine, and then dried over magnesium sulfate. After filtration and evaporation of the solvent under reduced pressure, the resulting residue was purified by silica gel column chromatography to give the desired compound (compound 33) (220 mg, yield 55%).

$^1$H-NMR (300 MHz, CD$_3$OD) δ: 1.60-1.70 (2H, m), 1.72 (6H, s), 1.98-2.06 (4H, m), 2.97-3.02 (2H, m), 3.87-3.92 (2H, m), 8.05 (1H, dd, J=1.5, 8.2 Hz), 8.21 (1H, d, J=1.5 Hz), 8.26 (1H, d, J=8.2 Hz).

Rf value (silica gel plate, developing solvent: ethyl acetate:methanol=3:1): 0.28.

MS(ESI): 464.5 ([M+H]$^+$).

(Fifth Step)

[Formula 20]

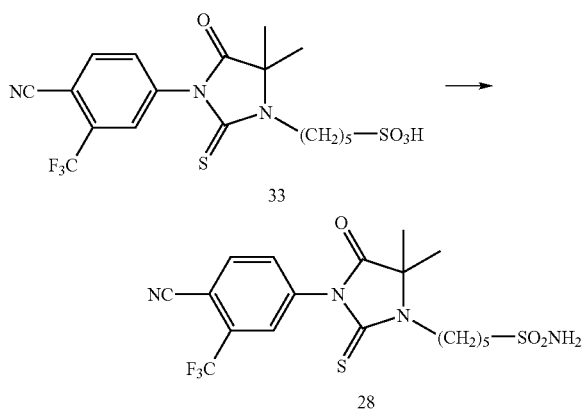

To compound 33 (80 mg), triethylamine (2.4 ml) was added and stirred at room temperature for 1 hour. This mixture was concentrated under reduced pressure to give a triethylammonium salt of compound 33 (86 mg). In a separate vessel, triphenylphosphine (93 mg) was dissolved in dichloromethane, followed by addition of thionyl chloride (0.0205 ml) at 0° C. To this reaction solution, the above triethylammonium salt of compound 33 (54 mg) in dichloromethane was added at 0° C. and stirred at room temperature for 4 hours. To the reaction solution, a mixed solvent of pentane and diethyl ether (1:1, 5 ml) was added, and the supernatant was separated and concentrated under reduced pressure. The resulting residue was dissolved in dichloromethane and aqueous ammonia (0.5 ml) was added thereto at 0° C., followed by stirring at 0° C. for 1 hour. After addition of water, the reaction mixture was extracted with dichloromethane and the organic layer was dried over magnesium sulfate. After filtration and concentration, the resulting residue was purified by thin-layer chromatography (ethyl acetate:n-hexane=1:1) to give the desired compound (compound 28) (7.6 mg).

$^1$H-NMR (300 MHz, CDCl$_3$) δ: 1.50-1.60 (2H, m), 1.58 (6H, s), 1.87-1.99 (4H, m), 3.15-3.21 (2H, m), 3.67-3.73 (2H, m), 4.61 (2H, brs), 7.77 (1H, dd, J=1.8, 8.1 Hz), 7.89 (1H, d, J=1.8 Hz), 7.95 (1H, d, J=8.1 Hz).

Rf value (silica gel plate, developing solvent: ethyl acetate:methanol=1:1): 0.083.

MS(ESI): 463.7 ([M+H]$^+$).

Example 8

[Formula 21]

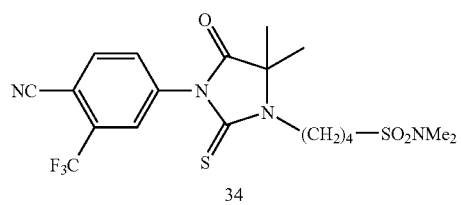

(First Step)

[Formula 22]

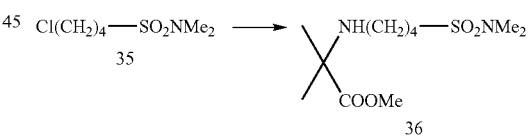

2-Aminoisobutyric acid methyl ester hydrochloride (1.0 g) and potassium carbonate (1.8 g) were dissolved in N,N-dimethylformamide (5 ml). To this solution, compound 35 (350 mg) and potassium iodide (50 mg) were added and stirred at 80° C. for 36 hours. After addition of water, the reaction mixture was extracted with ethyl acetate and the organic layer was dried over magnesium sulfate. After filtration and concentration, the resulting residue was purified by silica gel column chromatography to give the desired compound (compound 36) (119 mg, yield 24%).

$^1$H-NMR (300 MHz, CDCl$_3$) δ: 1.29 (6H, s), 1.56-1.61 (2H, m), 1.83-1.89 (2H, m), 2.48 (2H, t, J=7.1 Hz), 2.87 (6H, s), 2.90-2.95 (2H, m), 3.70 (3H, s).

Rf value (silica gel plate, developing solvent: ethyl acetate:n-hexane=1:2): 0.13.

(Second Step)

[Formula 23]

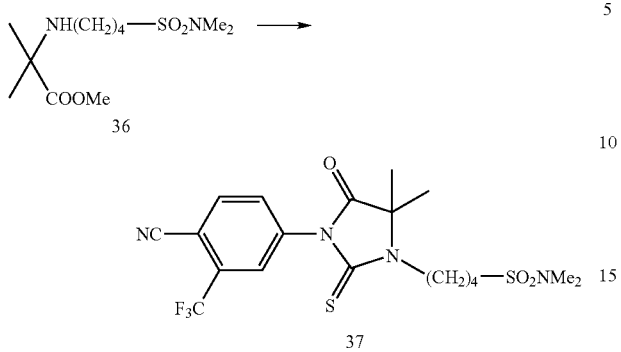

Compound 36 (115 mg) was dissolved in tetrahydrofuran (3 ml). To this solution, 4-cyano-3-trifluoromethylphenyl isothiocyanate (125 mg) and triethylamine (2 drops) were added and stirred at room temperature for 3 hours. The reaction solution was concentrated and recrystallized from ethyl acetate/n-hexane (1:1) to give the desired compound (compound 37) (98 mg, yield 54%).

$^1$H-NMR (300 MHz, CD$_3$OD) δ: 1.50 (6H, s), 1.76-1.94 (4H, m), 2.77 (6H, s), 3.00-3.05 (2H, m), 3.69-3.74 (2H, m), 7.81 (1H, dd, J=1.6, 8.4 Hz), 7.97 (1H, d, J=1.6 Hz), 8.02 (1H, d, J=8.4 Hz).

Rf value (silica gel plate, developing solvent: ethyl acetate:n-hexane=1:2): 0.48.

MS(ESI): 477.5 ([M+H]$^+$).

The following compounds were synthesized by the same method as in Example 8, except that in the first steps of Examples 9 to 14, tetra-n-butylammonium iodide was used instead of potassium iodide and a mixed solvent of acetonitrile and dimethylformamide was used as a solvent instead of dimethylformamide.

TABLE 3

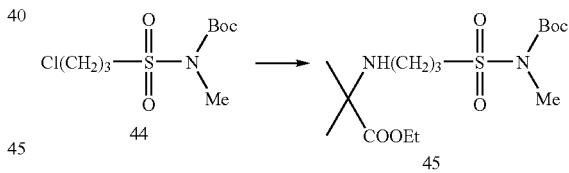

38

| Example | n | Data |
|---|---|---|
| 9 | 3 | Rf: 0.77 (dichloromethane:acetone = 20:1) MS(ESI): 485.5([M+Na]$^+$) |
| 10 | 5 | Rf: 0.18 (ethyl acetate:n-hexane = 1:1) MS(ESI): 491.5([M+H]$^+$) |
| 11 | 6 | Rf: 0.22 (ethyl acetate:n-hexane = 1:1) MS(ESI): 505.5([M+H]$^+$) |
| 12 | 7 | Rf: 0.64 (ethyl acetate:n-hexane = 2:1) MS(ESI): 519.4([M+H]$^+$) |
| 13 | 8 | Rf: 0.43 (ethyl acetate:n-hexane = 2:1) MS(ESI): 555([M+Na]$^+$) |
| 14 | 9 | Rf: 0.76 (ethyl acetate:n-hexane = 2:1) MS(ESI): 547.5([M+H]$^+$) |

Example 15

[Formula 24]

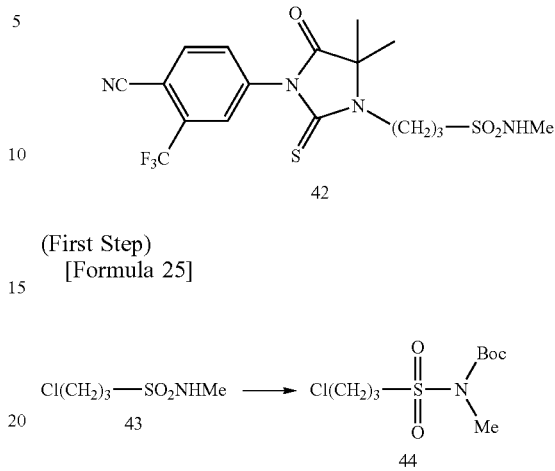

(First Step)

[Formula 25]

Cl(CH$_2$)$_3$—SO$_2$NHMe ⟶ Cl(CH$_2$)$_3$—S(=O)$_2$—N(Boc)(Me)

43                                44

Compound 43 (1.08 g), di-t-butyl dicarbonate (2.06 g) and N,N-dimethylaminopyridine (77 mg) were dissolved in acetonitrile (12.6 ml) and stirred at room temperature for 17 hours. After addition of water, the reaction mixture was extracted with dichloromethane and the organic layer was dried over magnesium sulfate. After filtration, the solvent was distilled off under reduced pressure to give the desired compound (compound 44) (1.65 g, yield 96%).

$^1$H-NMR (300 MHz, CDCl$_3$) δ: 1.55 (9H, s), 2.23-2.32 (2H, m), 3.21 (3H, s), 3.62-3.69 (4H, m).

Rf value (silica gel plate, developing solvent: ethyl acetate:n-hexane=1:2): 0.62.

(Second Step)

[Formula 26]

Cl(CH$_2$)$_3$—S(=O)$_2$—N(Boc)(Me) ⟶ (Me)$_2$C(COOEt)—NH(CH$_2$)$_3$—S(=O)$_2$—N(Boc)(Me)

44                                                                    45

2-Aminoisobutyric acid ethyl ester hydrochloride (592 mg) and potassium carbonate (1.02 g) were dissolved in a mixed solvent of acetonitrile (5 ml) and dimethylformamide (1 ml), followed by stirring at room temperature for 1 hour. After addition of compound 44 (800 mg) and sodium iodide (441 mg), the reaction mixture was stirred at 80° C. to 90° C. for 22 hours. After cooling, water was added and the reaction mixture was extracted with ethyl acetate. The organic layer was washed with brine and dried over magnesium sulfate. After filtration and evaporation of the solvent under reduced pressure, the resulting residue was purified by silica gel column chromatography (developing solvent: ethyl acetate:n-hexane=1:1) to give the desired compound (compound 45) (813 mg, yield 75%).

$^1$H-NMR (300 MHz, CDCl$_3$) δ: 1.27 (3H, t, J=7.1 Hz), 1.28 (6H, s), 1.54 (9H, s), 1.87-1.92 (2H, m), 2.59 (2H, t, J=6.5 Hz), 3.19 (3H, s), 3.54-3.59 (2H, m), 4.16 (2H, q, J=7.1 Hz).

Rf value (silica gel plate, developing solvent: ethyl acetate:n-hexane=1:1): 0.32.

(Third Step)

[Formula 27]

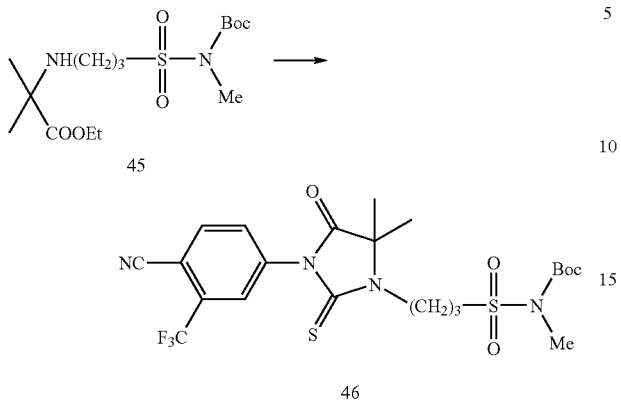

4-Cyano-3-trifluoromethylphenyl isothiocyanate (274 mg) was dissolved in tetrahydrofuran (5.5 ml). To this solution, compound 45 (400 mg) and triethylamine (0.034 ml) were added and stirred at room temperature for 2 hours. The reaction solution was concentrated under reduced pressure and then purified by silica gel column chromatography (developing solvent: ethyl acetate:n-hexane=1:3) to give the desired compound (compound 46) (624 mg).

$^1$H-NMR (300 MHz, CDCl$_3$) δ: 1.54 (9H, s), 1.62 (6H, s), 2.35-2.40 (2H, m), 3.23 (3H, s), 3.60 (2H, t, J=7.1 Hz), 3.88-3.93 (2H, m), 7.77 (1H, dd, J=1.8, 8.1 Hz), 7.89 (1H, d, J=1.8 Hz), 7.96 (1H, d, J=8.1 Hz).

Rf value (silica gel plate, developing solvent: ethyl acetate:n-hexane=1:1): 0.47.

(Fourth Step)

[Formula 28]

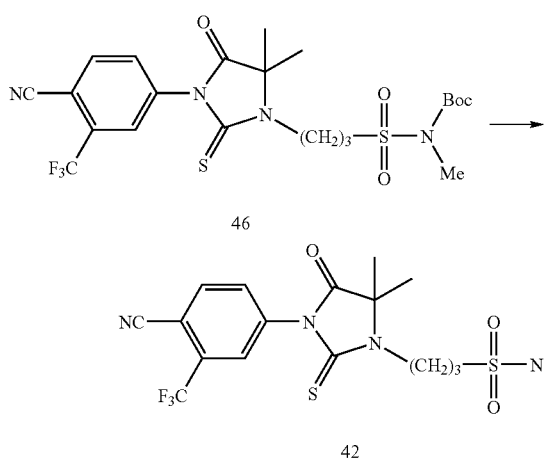

Compound 46 (300 mg) was dissolved in dichloromethane (2.7 ml) and cooled to 0° C. To this solution, trifluoroacetic acid (0.421 ml) was added dropwise and stirred at room temperature for 5.5 hours. The reaction solution was purified by silica gel column chromatography (developing solvent: ethyl acetate:n-hexane=1:1 to ethyl acetate:n-hexane:dichloromethane=1:1:1) to give the desired compound (compound 42) (235 mg, yield 96%).

$^1$H-NMR (300 MHz, CDCl$_3$) δ: 1.62 (6H, s), 2.33-2.39 (2H, m), 2.84 (3H, d, J=5.2 Hz), 3.16 (2H, t, J=7.1 Hz), 3.89-3.94 (2H, m), 4.35 (1H, q, J=5.2 Hz), 7.77 (1H, dd, J=1.7, 8.4 Hz), 7.90 (1H, d, J=1.7 Hz), 7.96 (1H, d, J=8.4 Hz).

Rf value (silica gel plate, developing solvent: ethyl acetate:n-hexane=1:1): 0.18.

MS(ESI$^-$): 447.1 ([M−H]$^-$).

The following compounds were synthesized by the same method as in Example 15.

TABLE 4

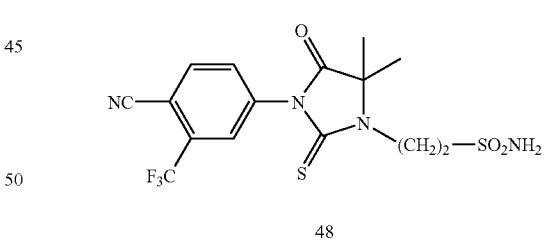

| Example No. | n | Data |
|---|---|---|
| 16 | 4 | Rf: 0.32 (dichloromethane:methanol = 30:1) |
| | | MS(ESI): 461.0([M−H]$^-$) |
| 17 | 5 | Rf: 0.12 (n-hexane:ethyl acetate = 1:2) |
| | | MS(ESI): 477.1([M+H]$^+$) |

Example 18

[Formula 29]

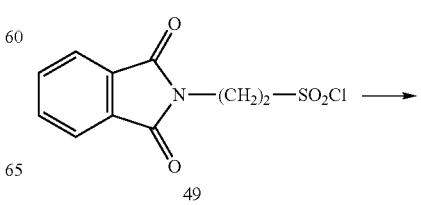

(First Step)

[Formula 30]

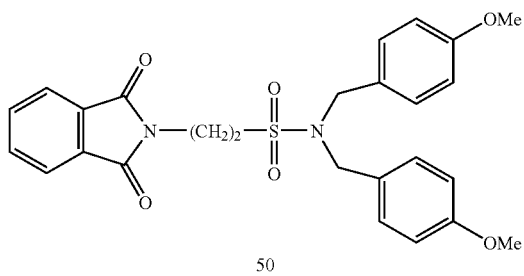

50

Bis (4-methoxybenzyl)amine (900 mg) was dissolved in dichloromethane (20 ml) and cooled to 0° C. To this solution, triethylamine (1.02 ml) was added and compound 49 (1.05 g) was added in small portions, followed by stirring at room temperature for 3 hours. After addition of water, the reaction mixture was extracted with dichloromethane. The organic layer was washed with brine and dried over magnesium sulfate. After filtration and evaporation of the solvent under reduced pressure, the resulting residue was purified by silica gel column chromatography (developing solvent: ethyl acetate:n-hexane=1:1 to ethyl acetate) to give the desired compound (compound 50) (1.4 g, yield 81%).

$^1$H-NMR (300 MHz, CDCl$_3$) δ: 3.24 (2H, t, J=6.8 Hz), 3.81 (6H, s), 4.10-4.14 (2H, m), 4.29 (4H, s), 6.88 (4H, d, J=8.7 Hz), 7.23 (4H, d, J=8.7 Hz), 7.73 (2H, dd, J=3.1, 5.3 Hz), 7.87 (2H, dd, J=3.1, 5.3 Hz).

Rf value (silica gel plate, developing solvent: ethyl acetate:n-hexane=1:1): 0.24.

(Second Step)
[Formula 31]

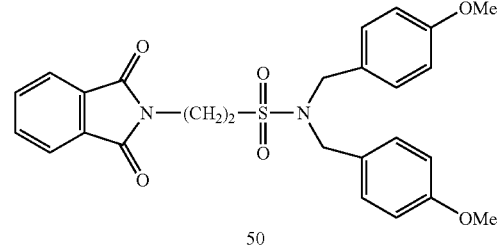

50

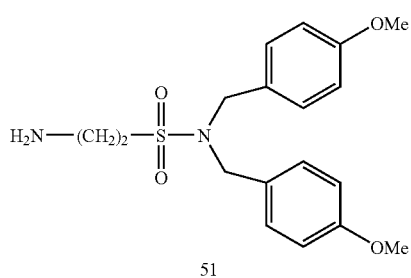

51

Compound 50 (1.4 g) was suspended in ethanol (15 ml). To this suspension, hydrazine monohydrate (0.151 ml) was added and stirred overnight at room temperature. The reaction solution was filtered and the filtrate was concentrated under reduced pressure. The resulting residue was purified by silica gel column chromatography (developing solvent: dichloromethane:methanol=100:1 to 50:1 to 20:1) to give the desired compound (compound 51) (460 mg, yield 45%).

$^1$H-NMR (300 MHz, CDCl$_3$) δ: 2.96 (2H, t, J=6.5 Hz), 3.16 (2H, t, J=6.5 Hz), 3.82 (6H, s), 4.27 (4H, s), 6.89 (4H, d, J=8.5 Hz), 7.22 (4H, d, J=8.5 Hz).

Rf value (silica gel plate, developing solvent: dichloromethane:methanol=10:1): 0.41.

(Third Step)
[Formula 32]

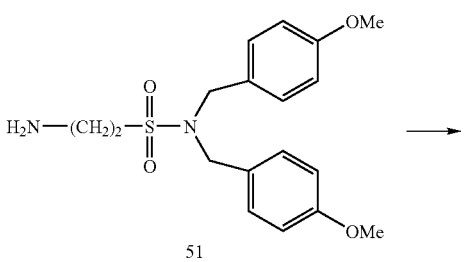

51

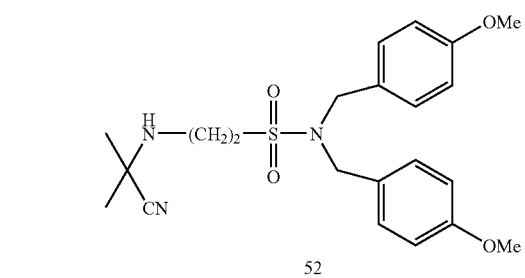

52

Compound 51 (450 mg) was dissolved in methanol (5 ml). To this solution, acetone cyanohydrin (0.136 ml) was added and stirred overnight at room temperature. After further addition of acetone cyanohydrin (0.226 ml), stirring was continued at 40° C. to 50° C. for an additional 3 hours. The reaction solution was concentrated under reduced pressure and purified by silica gel chromatography (developing solvent: dichloromethane:methanol=50:1) to give the desired compound (compound 52) (330 mg, yield 62%).

$^1$H-NMR (300 MHz, CDCl$_3$) δ: 1.44 (6H, s), 1.95 (1H, brs), 3.00-3.16 (4H, m), 3.82 (6H, s), 4.30 (4H, s), 6.89 (4H, d, J=8.7 Hz), 7.23 (4H, d, J=8.7 Hz).

Rf value (silica gel plate, developing solvent: dichloromethane:methanol=20:1): 0.67.

(Fourth Step)
[Formula 33]

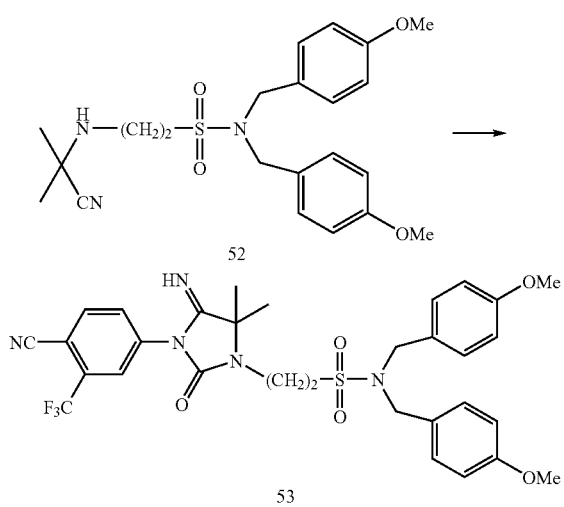

Compound 52 (220 mg) was dissolved in tetrahydrofuran (4.5 ml). To this solution, triethylamine (0.014 ml) and 4-cyano-3-trifluoromethylphenyl isothiocyanate (116 mg) were added and stirred at room temperature for 3 hours. The reaction solution was concentrated under reduced pressure and purified by silica gel column chromatography (developing solvent: dichloromethane:methanol=40:1) to give the desired compound (compound 53) (259 mg, yield 77%).

$^1$H-NMR (300 MHz, CDCl$_3$) δ: 1.55 (6H, s), 3.37-3.42 (2H, m), 3.81 (6H, s), 4.01-4.06 (2H, m), 4.29 (4H, s), 6.88 (4H, d, J=8.8 Hz), 7.25 (4H, d, J=8.8 Hz), 7.53-7.93 (4H, m).

Rf value (silica gel plate, developing solvent: dichloromethane:methanol=20:1): 0.24.

(Fifth Step)
[Formula 34]

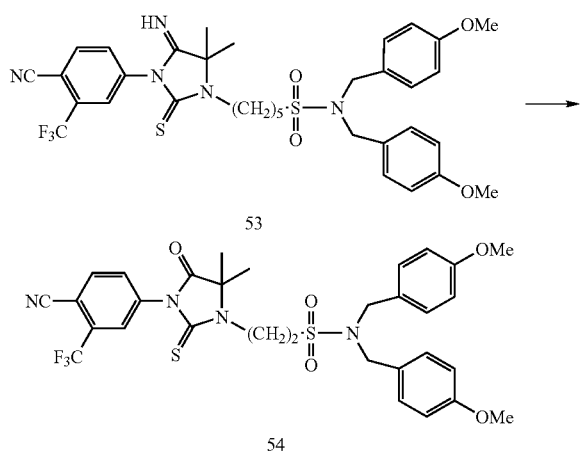

Compound 53 (259 mg) was dissolved in 1,4-dioxane (2.5 ml), followed by addition of 6N—HCl (2.5 ml). The resulting mixture was heated under reflux for 1 hour. After cooling, water was added and the reaction mixture was extracted with dichloromethane. The organic layer was washed with brine and dried over magnesium sulfate. After filtration and concentration under reduced pressure, the resulting residue was purified by silica gel column chromatography (developing solvent: ethyl acetate:n-hexane =1:2 to 1:1) to give the desired compound (compound 54) (144 mg, yield 56%).

$^1$H-NMR (300 MHz, CDCl$_3$) δ: 1.54 (6H, s), 3.37 -3.39 (2H, m), 3.81 (6H, s), 4.04-4.07 (2H, m), 4.30 (4H, s), 6.89 (4H, d, J=8.9 Hz), 7.25 (4H, d, J=8.9 Hz), 7.75 (1H, dd, J=8.5, 2.0 Hz), 7.88 (1H, d, J=2.0 Hz), 7.96 (1H, d, J=8.5 Hz).

Rf value (silica gel plate, developing solvent: ethyl acetate:n-hexane=1:1): 0.21.

(Sixth Step)
[Formula 35]

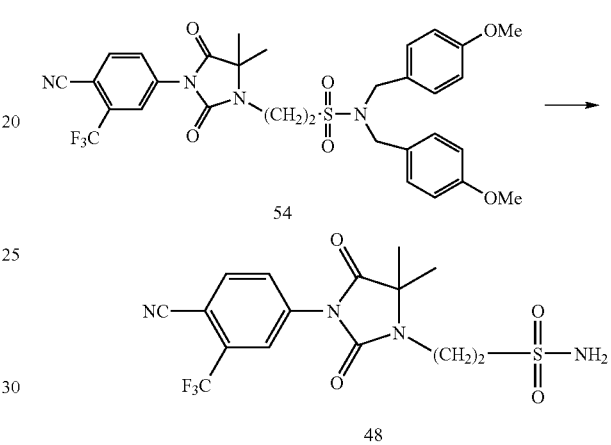

Compound 54 (140 mg), trifluoroacetic acid (1 ml) and anisole (0.02 ml) were mixed and stirred at room temperature for 2 hours, followed by heating under reflux for 1 hour. After cooling, water was added and the reaction mixture was extracted with ethyl acetate. The organic layer was washed with brine and dried over magnesium sulfate. After filtration and concentration under reduced pressure, the resulting residue was purified by silica gel column chromatography (developing solvent: ethyl acetate:n-hexane=1:1 to 2:1 to 4:1) to give the desired compound (compound 48) (64 mg, yield 72%).

$^1$H-NMR (300 MHz, CDCl$_3$) δ: 1.64 (6H, s), 3.67-3.72 (2H, m), 4.17-4.22 (2H, m), 4.88 (2H, brs), 7.76 (1H, dd, J=1.8, 8.5 Hz), 7.88 (1H, d, J=1.8 Hz), 7.97 (1H, d, J=8.5 Hz).

Rf value (silica gel plate, developing solvent: ethyl acetate:n-hexane=3:1): 0.21.

MS(ESI$^-$): 419.1 ([M–H]$^-$).

Preparation of Cells Used in Test Examples

Preparation of 11A11B2 Cells

HeLa cells (purchased from Dai-Nippon Seiyaku K. K.) were cultured overnight in Dulbecco's Modified Eagle Medium containing no phenol red, but containing 3% charcoal-treated fetal bovine serum (hereafter referred to as DCC-FBS) (this medium is hereafter referred to as phenol-red-free DMEM). An MMTV-Luc-Hyg vector (reporter plasmid with Mouse tumor Long terminal repeat, containing an androgen response element and a hygromycin resistance gene: a vector obtained by substituting the chloramphenicol acetyl transferease gene of a GM-CAT vector (A.T.C.C No. 67282) purchased from the A.T.C.C. for the firefly luciferase gene, and inserting a hygromycin resistance gene), and pSG5-hAR-neo (human androgen receptor expression vector: a vector having an androgen receptor gene under the control of the SV40 promoter, and having a neomycin resistance gene inserted as a drug resistance gene) were transfected into the HeLa cells using an FuGENE™ 6 Transfection Reagent (obtained from Roche).

A clone in which transcription activity was elevated in a dose-dependent manner by dihydrotestosterone (DHT) was obtained by culturing the transfected cells in DMEM containing 500 μg/mL neomycin, 300 μg/mL hygromycin and 10% FBS. The clone cells thus obtained (11A11B2 cells) were maintained and propagated using DMEM containing 400 μg/mL neomycin, 200 μg/mL hygromycin and 10% FBS, and were propagated using phenol-red-free DMEM containing 10% DCC-FBS three to four days prior to the performance of an androgen receptor reporter gene assay.

Test Example 1

Investigation of Agonist Effects of Compounds of the Examples and Compounds of the Comparative Examples The 11A11B2 cells were inoculated in a white clear-bottomed 96-well microplate (COSTAR) so that the cell concentration was $1.0 \times 10^4$/well, and were cultured overnight using phenol-red-free DMEM containing 3% DCC-FBS (hereafter referred to as the assay medium). Samples of the assay medium containing the compounds of the examples and compounds of the comparative examples were added so that the final concentrations of the compounds of the examples and compounds of the comparative examples were 1, 10, 100, 1,000 and 10,000 nmol/L (however, in the case of the compounds of Examples 1 and 2, the compounds were added so that the final concentrations were 1, 10, 100, 1,000, 10,000 and 100,000 nmol/L), and the cells were cultured for 48 hours, after which the transcription activity value was measured. The transcription activity was measured using a Bright-Glo™ Luciferase Assay System (Promega).

The transcription activity rates of the compounds of the examples were calculated from the transcription activity measured by the abovementioned method, with the transcription activity value obtained at 0.1 nmol/L DHT taken as 100%, and the transcription activity value in the case of the assay medium alone taken as 0%. The compound concentration showing a transcription activity of 5% (EC5 value) was calculated from a linear equation for two points on either side of 5%.

Test Example 2

Investigation of Antagonist Effects of Compounds of the Examples and Compounds of the Comparative Examples The 11A11B2 cells were inoculated in a white clear-bottomed 96-well microplate (COSTAR) so that the cell concentration was $1.0 \times 10^4$/well, and were cultured overnight using phenol-red-free DMEM containing 3% DCC-FBS (hereafter referred to as the assay medium). The assay medium containing DHT was added so that the final concentration of DHT was 0.1 nmol/L, and samples of the assay medium containing the compounds of the examples or compounds of the comparative examples were added so that the final concentrations of the compounds of the examples or compounds of the comparative examples were 1, 10, 100, 1,000 and 10,000 nmol/L, respectively. After culturing for 48 hours, the transcription activity values were measured. The transcription activity was measured using a Bright-Glo™ Luciferase Assay System (Promega).

The transcription activity rates of the compounds of the examples were calculated from the transcription activity measured by the abovementioned method, with the transcription activity value obtained at 0.1 nmol/L DHT taken as 100%, and the transcription activity value in the case of the assay medium alone taken as 0%.

In the present test system (Test Example 2), there were cases in which the transcription activity dropped to 50% in compounds showing both antagonist activity and agonist activity. Accordingly, the value obtained by subtracting the transcription activity rate of Test Example 1 (Investigation of Agonist Activity) from the transcription activity rate of Test Example 2 (Investigation of Antagonist Activity) was used to calculate the compound concentration at which a transcription activity of 50% was shown (IC50 value). The IC50 value was calculated from a linear equation for two points on either side of 50%.

The results of Test Examples 1 and 2 are shown in Table 1.

Table 5

TABLE 1

| Compound | EC5 (nM) | IC50 (nM) | EC5/IC50 |
|---|---|---|---|
| Compound of Example 1 | 20000 | 200 | 100 |
| Compound of Example 2 | >100000 | 600 | >170 |
| Compound of Example 3 | 3000 | 200 | 15 |
| Compound of Example 7 | >10000 | 900 | >11 |
| Compound of Example 8 | 2000 | 100 | 20 |
| Compound of Example 10 | 2000 | 200 | 10 |
| Compound of Example 16 | >10000 | 700 | >14 |
| Compound of Example 18 | 7000 | 600 | 12 |
| Comparative Example 1 | 0.08 | 1 | 0.080 |
| Comparative Example 2 (BP-139) | 3000 | 800 | 3.8 |
| Comparative Example 3 (bicalutamide) | 20 | 300 | 0.067 |
| Comparative Example 4 (hydroxyflutamide) | 10 | 100 | 0.1 |

Comparative Example 1: Compound of Example 12 in Japanese Patent Application Laid-Open No. 4-308579 (4-(5-oxo-2-thioxo-3,4,4-trimethyl-1-imidazolidinyl)-2-trifluoromethylbenzonitrile)

Comparative Example 2: Compound of Example 15 in Japanese Patent Publication No. 10-510845 ((4-[3'-(2"-N-acetylaminoethyl)-4',4'-dimethyl-5'-oxo-2'-thioxo-1'-imidazolidinyl]-2-trifluoromethylbenzonitrile)

Comparative Examples 3 and 4 are universally known compounds, and can be manufactured by universally known methods.

The effect as an anti-androgen agent with reduced agonist activity can be judged by comparing the EC5/IC50 values. Specifically, compounds that have a high EC5/IC50 value are compounds that have a more desirable effect. In concrete terms, it is desirable that the EC5/IC50 value be 5 or greater, preferably 10 or greater, and even more preferably 20 or greater.

In Test Examples 1 and 2, it was confirmed that the compounds expressed by formula (I) of the present invention have EC5/IC50 values that are clearly higher than those of the compounds of the comparative examples.

INDUSTRIAL APPLICABILITY

It is expected that the compounds of the present invention expressed by formula (I) will act as anti-androgen agents that show no manifestation of androgen resistance due to long-term administration, and/or side effects such as liver toxicity or the like. Furthermore, it is expected that these compounds will be useful in drug compositions, e. g., therapeutic agents for diseases such as prostate cancer, benign prostatic hypertrophy, male pattern baldness, sexual precociousness, common acne, seborrhea, hypertrichosis and the like. Furthermore, it is expected that the compounds of the present invention expressed by general formula (I) will prevent or delay the onset of diseases such as prostate cancer, benign prostatic hypertrophy, male pattern baldness, sexual precociousness, common acne, seborrhea, hypertrichosis and the like, if these compounds are administered in advance. Accordingly, it is expected that these compounds will act as prophylactic agents for such diseases.

The invention claimed is:

1. A compound represented by formula (I):

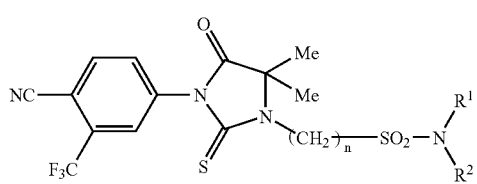

wherein n is an integer selected from 1 to 20, and $R^1$ and $R^2$, which may be the same or different, each represent a hydrogen atom or a linear or branched $C_1$-$C_6$ alkyl group, or a salt, a prodrug or a solvate thereof.

2. A compound according to claim 1 or a salt, a prodrug or a solvate thereof, wherein n is an integer selected from 1 to 10.

3. A compound according to claim 1 or a salt, a prodrug or a solvate thereof, wherein $R^1$ and $R^2$ are each a hydrogen atom.

4. A compound according to claim 1 or a salt, a prodrug or a solvate thereof, wherein at least one of $R^1$ and $R^2$ is a methyl group.

5. A compound according to claim 1, which is selected from the group consisting of:

4-[3'-(3"-aminosulfonylpropyl)-4',4'-dimethyl-5'-oxo-2'-thioxo-1'-imidazolidinyl]-2-trifluoromethylbenzonitrile;

4-[3'-(4"-aminosulfonylbutyl)-4',4'-dimethyl-5'-oxo-2'-thioxo-1'-imidazolidinyl]-2-trifluoromethylbenzonitrile;

4-[3'-(6"-aminosulfonylhexyl)-4',4'-dimethyl-5'-oxo-2'-thioxo-1'-imidazolidinyl]-2-trifluoromethylbenzonitrile;

4-[3'-(7"-aminosulfonylheptyl)-4',4'-dimethyl-5'-oxo-2'-thioxo-1'-imidazolidinyl]-2-trifluoromethylbenzonitrile;

4-[3'-(8"-aminosulfonyloctyl)-4',4'-dimethyl-5'-oxo-2'-thioxo-1'-imidazolidinyl]-2-trifluoromethylbenzonitrile;

4-[3'-(9"-aminosulfonylnonyl)-4',4'-dimethyl-5'-oxo-2'-thioxo-1'-imidazolidinyl]-2-trifluoromethylbenzonitrile;

4-[3'-(5"-aminosulfonylpentyl)-4',4'-dimethyl-5'-oxo-2'-thioxo-1'-imidazolidinyl]-2-trifluoromethylbenzonitrile;

4-[3'-(4"-N,N-dimethylaminosulfonylbutyl)-4',4'-dimethyl-5'-oxo-2'-thioxo-1'-imidazolidinyl]-2-trifluoromethylbenzonitrile;

4-[3'-(3"-N,N-dimethylaminosulfonylpropyl)-4',4'-dimethyl-5'-oxo-2'-thioxo-1'-imidazolidinyl]-2-trifluoromethylbenzonitrile;

4-[3'-(5"-N,N-dimethylaminosulfonylpentyl)-4',4'-dimethyl-5'-oxo-2'-thioxo-1'-imidazolidinyl]-2-trifluoromethylbenzonitrile;

4-[3'-(6"-N,N-dimethylaminosulfonylhexyl)-4',4'-dimethyl-5'-oxo-2'-thioxo-1'-imidazolidinyl]-2-trifluoromethylbenzonitrile;

4-[3'-(7"-N,N-dimethylaminosulfonylheptyl)-4',4'-dimethyl-5'-oxo-2'-thioxo-1'-imidazolidinyl]-2-trifluoromethylbenzonitrile;

4-[3'-(8"-N,N-dimethylaminosulfonyloctyl)-4',4'-dimethyl-5'-oxo-2'-thioxo-1'-imidazolidinyl]-2-trifluoromethylbenzonitrile;

4-[3'-(9"-N,N-dimethylaminosulfonylnonyl)-4',4'-dimethyl-5'-oxo-2'-thioxo-1'-imidazolidinyl]-2-trifluoromethylbenzonitrile;

4-[3'-(3"-N-methylaminosulfonylpropyl)-4',4'-dimethyl-5'-oxo-2'-thioxo-1'-imidazolidinyl]-2-trifluoromethylbenzonitrile;

4-[3'-(4"-N-methylaminosulfonylbutyl)-4',4'-dimethyl-5'-oxo-2'-thioxo-1'-imidazolidinyl]-2-trifluoromethylbenzonitrile;

4-[3'-(5"-N-methylaminosulfonylpentyl)-4',4'-dimethyl-5'-oxo-2'-thioxo-1'-imidazolidinyl]-2-trifluoromethylbenzonitrile; and 4-[3'-(2"-aminosulfonylethyl)-4',4'-dimethyl-5'-oxo-2'-thioxo-1'-imidazolidinyl]-2-trifluoromethylbenzonitrile or a salt, a prodrug or a solvate thereof.

6. A pharmaceutical composition which comprises the compound according to claim 1 or a salt, a prodrug or a solvate thereof as an active ingredient.

7. A process for preparing a compound represented by formula (I):

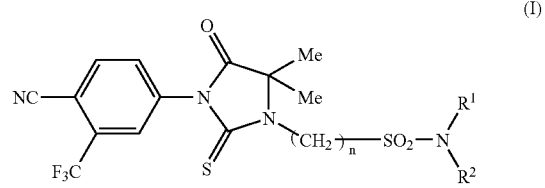

wherein n is an integer selected from 1 to 20, and $R^1$ and $R^2$, which may be the same or different, each represent a hydrogen atom or a linear or branched $C_1$-$C_6$ alkyl group, which comprises the steps of:

reacting a compound represented by formula (II):

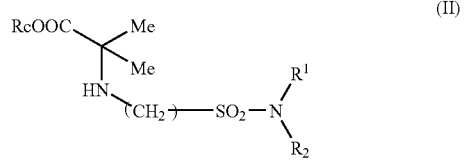

wherein
n is an integer selected from 1 to 20;
Ra and Rb, which may be the same or different, are each selected from the group consisting of a linear or branched $C_1$-$C_6$ alkyl group substituted with one or more $W^1$, a linear or branched $C_1$-$C_6$ alkylcarbonyl group which may be substituted with one or more $W^1$, an arylcarbonyl group which may be substituted with one or more $W^2$, a linear or branched $C_1$-$C_6$ alkoxycarbonyl group which may be substituted with one or more $W^1$, an aryloxycarbonyl group which may be substituted with one or more $W^2$, a linear or branched $C_1$-$C_6$ alkylaminocarbonyl group which may be substituted with one or more $W^1$, a linear or branched $C_1$-$C_6$ dialkylaminocarbonyl group which may be substituted with one or more $W^1$, a linear or branched $C_1$-$C_6$ alkylsulfonyl group which may be substituted with one or more $W^1$, an arylsulfonyl group which may be substituted with one or more $W^2$, and $R^1$ and $R^2$; or
Ra and Rb may be joined together to form a group =CH—$W^3$;
$W^1$ is a linear or branched $C_1$-$C_6$ alkoxy group, a linear or branched $C_1$-$C_6$ alkylthio group, a linear or branched $C_1$-$C_6$ alkylsulfinyl group, a linear or branched $C_1$-$C_6$ alkylsulfonyl group, an aryl group which may be substituted with one or more $W^2$, an aryloxy group which may be substituted with one or more $W^2$, or a $C_1$-$C_3$ aralkyloxy group which may be substituted with one or more $W^2$;
$W^2$ is a linear or branched $C_1$-$C_6$ alkyl group, a linear or branched $C_1$-$C_6$ alkoxy group, a linear or branched $C_1$-$C_6$ haloalkyl group, a halogen atom, a cyano group, or a nitro group;
$W^3$ is a linear or branched $C_1$-$C_6$ alkyl group, a linear or branched $C_1$-$C_6$ alkoxy group, a linear or branched $C_1$-$C_6$ alkylamino group, or a linear or branched $C_1$-$C_6$ dialkylamino group;
$R^1$ and $R^2$ are as defined in claim 1; and
Rc is a linear or branched $C_1$-$C_6$ alkyl group with 4-cyano-3-trifluoromethylphenyl isothiocyanate to obtain a compound represented by formula (III):

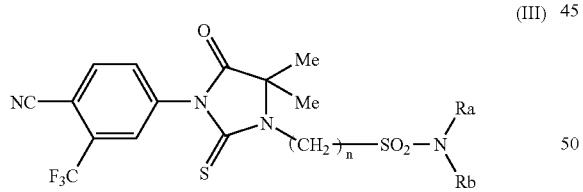

(III)

wherein n, Ra and Rb are as defined above; and
a deprotection in cases where at least one of the groups Ra and Rb is other than $R^1$ and $R^2$.

8. A compound represented by formula (II) or (II-a):

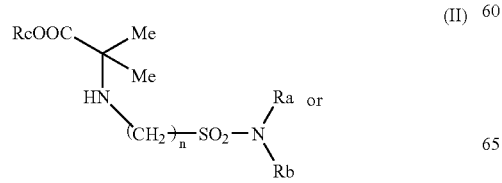

(II)

or

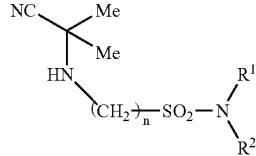

(II-a)

wherein n is an integer selected from 1 to 20;
Ra and Rb, which may be the same or different, are each selected from the group consisting of a linear or branched $C_1$-$C_6$ alkyl group substituted with one or more $W^1$, a linear or branched $C_1$-$C_6$ alkylcarbonyl group which may be substituted with one or more $W^1$, an arylcarbonyl group which may be substituted with one or more $W^2$, a linear or branched $C_1$-$C_6$ alkoxycarbonyl group which may be substituted with one or more $W^1$, an aryloxycarbonyl group which may be substituted with one or more $W^2$, a linear or branched $C_1$-$C_6$ alkylaminocarbonyl group which may be substituted with one or more $W^1$, a linear or branched $C_1$-$C_6$ dialkylaminocarbonyl group which may be substituted with one or more $W^1$, a linear or branched $C_1$-$C_6$ alkylsulfonyl group which may be substituted with one or more $W^1$, an arylsulfonyl group which may be substituted with one or more $W^2$, and $R^1$ and $R^2$; or
Ra and Rb may be joined together to form a group =CH—$W^3$;
$W^1$ is a linear or branched $C_1$-$C_6$ alkoxy group, a linear or branched $C_1$-$C_6$ alkylthio group, a linear or branched $C_1$-$C_6$ alkylsulfinyl group, a linear or branched $C_1$-$C_6$ alkylsulfonyl group, an aryl group which may be substituted with one or more $W^2$, an aryloxy group which may be substituted with one or more $W^2$, or a $C_1$-$C_3$ aralkyloxy group which may be substituted with one or more $W^2$;
$W^2$ is a linear or branched $C_1$-$C_6$ alkyl group, a linear or branched $C_1$-$C_6$ alkoxy group, a linear or branched $C_1$-$C_6$ haloalkyl group, a halogen atom, a cyano group, or a nitro group;
$W^3$ is a linear or branched $C_1$-$C_6$ alkyl group, a linear or branched $C_1$-$C_6$ alkoxy group, a linear or branched $C_1$-$C_6$ alkylamino group, or a linear or branched $C_1$-$C_6$ dialkylamino group;
Rc is a linear or branched $C_1$-$C_6$ alkyl group; and
$R^1$ and $R^2$, which may be the same or different, each represent a hydrogen atom or a linear or branched $C_1$-$C_6$ alkyl group.

9. A compound represented by formula (III):

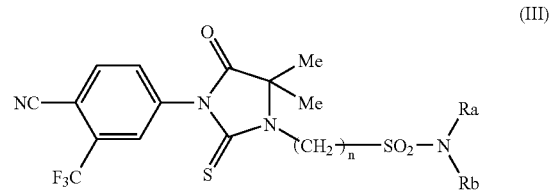

(III)

wherein n is an integer selected from 1 to 20;
Ra and Rb, which may be the same or different, are each selected from the group consisting of a linear or branched $C_1$-$C_6$ alkyl group substituted with one or more $W^1$, a linear or branched $C_1$-$C_6$ alkylcarbonyl group which may be substituted with one or more $W^1$, an arylcarbonyl group which may be substituted with one or more $W^2$, a linear or branched $C_1$-$C_6$ alkoxycarbonyl group which may be substituted with one or more $W^1$, an aryloxycarbonyl group which may be substituted with one or more $W^2$, a linear or branched $C_1$-$C_6$ alkylaminocarbonyl group which may be substituted with one or more $W^1$, a linear or branched $C_1$-$C_6$ dialkylaminocarbonyl group which may be substituted with one or more $W^1$, a linear or branched $C_1$-$C_6$ alkylsulfonyl group which may be substituted with one or more $W^1$, an arylsulfonyl group which may be substituted with one or more $W^2$, and $R^1$ and $R^2$; or Ra and Rb may be joined together to form a group =CH—$W^3$;

$W^1$ is a linear or branched $C_1$-$C_6$ alkoxy group, a linear or branched $C_1$-$C_6$ alkylthio group, a linear or branched $C_1$-$C_6$ alkylsulfinyl group, a linear or branched $C_1$-$C_6$ alkylsulfonyl group, an aryl group which may be substituted with one or more $W^2$, an aryloxy group which may be substituted with one or more $W^2$, or a $C_1$-$C_3$ aralkyloxy group which may be substituted with one or more $W^2$;

$W^2$ is a linear or branched $C_1$-$C_6$ alkyl group, a linear or branched $C_1$-$C_6$ alkoxy group, a linear or branched $C_1$-$C_6$ haloalkyl group, a halogen atom, a cyano group, or a nitro group; and $W^3$ is a linear or branched $C_1$-$C_6$ alkyl group, a linear or branched $C_1$-$C_6$ alkoxy group, a linear or branched $C_1$-$C_6$ alkylamino group, or a linear or branched $C_1$-$C_6$ dialkylamino group.

10. A pharmaceutical composition which comprises the compound according to claim 2 or a salt, a prodrug or a solvate thereof as an active ingredient.

11. A pharmaceutical composition which comprises the compound according to claim 3 or a salt, a prodrug or a solvate thereof as an active ingredient.

12. A pharmaceutical composition which comprises the compound according to claim 4 or a salt, a prodrug or a solvate thereof as an active ingredient.

13. A pharmaceutical composition which comprises the compound according to claim 5 or a salt, a prodrug or a solvate thereof as a active ingredient.

* * * * *

UNITED STATES PATENT AND TRADEMARK OFFICE
CERTIFICATE OF CORRECTION

| | | |
|---|---|---|
| PATENT NO. | : 7,271,188 B2 | Page 1 of 1 |
| APPLICATION NO. | : 10/560281 | |
| DATED | : September 18, 2007 | |
| INVENTOR(S) | : Kazutaka Tachibana et al. | |

It is certified that error appears in the above-identified patent and that said Letters Patent is hereby corrected as shown below:

Title Page
At section (73) Assignee, correct the incorrect assignee name by deleting "Chugai Seikayu Kabushiki Kaisha, Tokyo (JP)" and insert --Chugai Seiyaku Kabushiki Kaisha, Tokyo (JP)--.

Signed and Sealed this
Fourth Day of October, 2011

David J. Kappos
*Director of the United States Patent and Trademark Office*